(12) United States Patent
Zheng et al.

(10) Patent No.: US 9,464,277 B2
(45) Date of Patent: *Oct. 11, 2016

(54) COMPOSITIONS AND METHODS FOR OXYGENATION OF NUCLEIC ACIDS CONTAINING 5-METHYLPYRIMIDINE

(71) Applicant: New England Biolabs, Inc., Ipswich, MA (US)

(72) Inventors: Yu Zheng, Topsfield, MA (US); Lana Saleh, Hamilton, MA (US); June Pais, Ipswich, MA (US); Nan Dai, Gloucester, MA (US); Richard J. Roberts, Wenham, MA (US); Ivan R. Correa, Jr., Ipswich, MA (US); Megumu Mabuchi, Beverly, MA (US); Romualdas Vaisvila, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/691,088

(22) Filed: Apr. 20, 2015

(65) Prior Publication Data

US 2015/0218530 A1    Aug. 6, 2015

Related U.S. Application Data

(63) Continuation of application No. 13/827,087, filed on Mar. 14, 2013, now Pat. No. 9,040,239.

(60) Provisional application No. 61/724,041, filed on Nov. 8, 2012, provisional application No. 61/723,427, filed on Nov. 7, 2012, provisional application No. 61/722,968, filed on Nov. 6, 2012, provisional application No. 61/611,295, filed on Mar. 15, 2012.

(51) Int. Cl.
| | | |
|---|---|---|
| C12N 9/02 | (2006.01) | |
| C12Q 1/68 | (2006.01) | |
| C07H 19/06 | (2006.01) | |
| C07H 21/00 | (2006.01) | |
| C12P 19/18 | (2006.01) | |
| C12P 19/30 | (2006.01) | |
| C12P 19/34 | (2006.01) | |
| C12N 9/10 | (2006.01) | |
| C12N 9/22 | (2006.01) | |
| C07K 14/47 | (2006.01) | |

(52) U.S. Cl.
CPC ............ *C12N 9/0069* (2013.01); *C07H 19/06* (2013.01); *C07H 21/00* (2013.01); *C07K 14/47* (2013.01); *C12N 9/1051* (2013.01); *C12N 9/22* (2013.01); *C12P 19/18* (2013.01); *C12P 19/30* (2013.01); *C12P 19/34* (2013.01); *C12Q 1/68* (2013.01); *C12Q 1/683* (2013.01); *C12Q 1/6806* (2013.01); *C12Q 1/6809* (2013.01); *C12Q 1/6827* (2013.01); *C07K 2319/80* (2013.01); *C07K 2319/81* (2013.01); *Y02P 20/52* (2015.11)

(58) Field of Classification Search
None
See application file for complete search history.

(56) References Cited

U.S. PATENT DOCUMENTS

2012/0301881 A1    11/2012 Zhu et al.

FOREIGN PATENT DOCUMENTS

WO    WO2011025819 A1    3/2011

OTHER PUBLICATIONS

Morera, et al., J. Mol. Biol., 292(3):717-730 (1999).
Borgaro, et al., Nucleic Acids Research, doi:10.1093/nar/gkt102 (2013).
Witkowski, et al, Biochemistry, 38, 11643-11650, 1999.
Wishart, et al, Journal of Biological Chemistry, 270, 26782-26785, 1995.
Broun, et al., Science, 282, 1315-1317, 1998.
Dai, et al., ChemBioChem, 14, 2144-2152, 2013.
Lorsbach, et al., Lukemia, 17, 637-641, 2003.

*Primary Examiner* — Kagnew H Gebreyesus
(74) *Attorney, Agent, or Firm* — New England Biolabs, Inc; Harriet M. Strimpel

(57) ABSTRACT

5-methylpyrimidine oxygenases and their use in the modification of nucleic acids are described.

19 Claims, 8 Drawing Sheets

FIG. 2B

```
Conservation:                          5                5           7   6    5  7  5                          9 6
290969988    33 IVAGISDENNTLDNLT------NCCESFVLDKLWHLNRSMYNKLDTIEEKTKNFKTY---AKYPSLA    91
290971192    87 PVKTITTNQSILHEN------DKCGPFVLDKLKHINKNMFNKLDNINEDTKNYIF---AKYPTLA   145
290999172   149 KCA------DSFR-FELVDTKV-KQIQALLHDTFQHIELANPKLFAKLSKLT-------ERGQTPVVC   202
290982775     6 ITS------DLK---TQLGEYLIGIVNPMLDETITAALEILSPHTINYLTSLP------HPYHILNNCIYPSTA    64
mYOX1       154 VTA------DLS---QELGQYLSEIVNPQINYYISKLLTCVSSRTINYLVSLN------DSYYALNNCLYPSTA   212
290988510    43 LFK----TNDTIFNELSSQFIKII-NLLKNYLEILKFGNNKMRKFLEKYN-----SSDFL---SIYPTVC    100
290987636   328 MCK------DNE---SEIGKVVNEIA-ELLSDHCRNLLRMCNERVYKKISELK-----EDKFF----APCIC   380
290971639    25 IAA------DNC---NKSGETIVENLLFKLGKIGSKLMEILSPFTMNFLSSLD-----PEIFLNHDLFPISA    82
Consensus_ss:     eee               hhhhhhhhhh hhhhhhhhhhhhhhhhhhhhhhhh         e          hh Conservation:         59                        76   9 9   7 7    5 5759  5   57 7                         6
290969988    92 LNLLCKEN--------YNGKVKPYRKHIDPNNNGMDVLMFFGKTFE--GGNLIVSYHYTNI-   142
290971192   146 LNVSHNEN--------YNISKKPYRKHTDGNDIGLGVLTYFGSEIIE-GGNLII--HIEN-   194
290999172   203 FNMIPTRNESVKEKFQGSYKSTDKVN--RPKTNHRDRNDMGISAMFYMGK-FG--GGSLQL--IRVNEHT   265
290982775    65 FNYLEPQI--------EKH---RIKNAHKDTRDATPSVLFYLGD-YDEKEGYLEF--PEQN-   111
mYOX1       213 FNSLKPSN--------DGH---RIRKPHKONLDITPSSLFYFGN-FQNTEGYLEL--TDKN-   259
290988510   101 FNFLDKSV--------DEN---RILIHPDKEDTGTSLIFYFGK--FK--GGAISF--PELN-   145
290987636   381 FNILEHD---------LES---RITKFHHDKMDYGVSVLFYGD-YS--RGNLNV--LDAGS-   425
290971639    83 TNFMIPG---------NKH---RILKPHKDNQDVGLCIIFYFGN-YN---APLEF--VNKG-   125
Consensus_ss:    eeeeee                          eeeeeeeeeeee                  ee         ee Conservation:        595655   5     5 9 9           9 6    75997   5
290969988   143 -DFRMFTLPIQSGDLVFLNSRIYHHKVTKV(3)VRCGLVFFAGLDHFSVRK---------------A   193
290971192   195 --LKVFNFPTQRRDLVFLNSKFYAHQVTKV(3)IRFGLVYFAGEAHFRVRN---------------   243
290999172   266 PKTLVH----IQAGDVLLRANKYRHAVSPT(68)KRFSFIFFAHRSHFKHSKVYCGMGRQALNAFKADHP   397
290982775   112 --CKVF----VKPGDLLLFFKGNKYKHQVAPI(3)TRLGLVYFAHKACKVM---------------   156
mYOX1       260 --CKVF----VQPGDVLFFKGNEYKHVVANT(3)WRIGLVYFAHKGSKTK---------------D   304
290988510   146 --FKLM----VQSADVLLFDGKNNLHAVESL(5)VRYSVVFFAHKADLGKTSY---------------   194
290987636   426 --SSTIV---TRPGDAVILRGNYYKHSVQNI(6)ARYSIVFFAHSTHFLKKYE---LSPAAKKAFLVDNP   492
290971639   126 ---SVFN---TERGDVLLMRGSHFRHVVKPV(1)MRISVLLFAHKSLKMN---------------P   178
Consensus_ss:    e      e       eeeee       eeeeee                  hhhhhh
```

COMPOSITIONS AND METHODS FOR OXYGENATION OF NUCLEIC ACIDS CONTAINING 5-METHYLPYRIMIDINE

REFERENCE TO RELATED APPLICATIONS

This application is a continuation of U.S. application Ser. No. 13/827,087 filed Mar. 14, 2013, now U.S. Pat. No. 9,040,239.

The entire disclosure of each of the following patent applications is hereby incorporated by reference into the present application: U.S. 61/611,295, filed Mar. 15, 2012; U.S. Application No. 61/722,968, filed Nov. 6, 2012; U.S. Application No. 61/723,427, filed Nov. 7, 2012; U.S. Application No. 61/724,041, filed Nov. 8, 2012; U.S. application Ser. No. 13/804,804, filed Mar. 14, 2013; U.S. application Ser. No. 13/826,395, filed Mar. 14, 2013; U.S. application Ser. No. 13/827,885, filed Mar. 14, 2013.

GOVERNMENT RIGHTS

This invention was made with government support under GM105132 awarded by the National Institutes of Health. The government has certain rights in the invention.

BACKGROUND 5-methylcytosine (5-mC) has been linked to gene expression and its distribution in the genome plays an important role in epigenetics. In 2009, two groups independently discovered that an oxidized form of 5-mC, 5-hydroxymethylcytosine (5-hmC), exists in human and mouse DNA, and is especially enriched in the neuronal tissues as well as embryonic stem cells. Three enzymes named TET1/2/3 have been shown in human and mouse to be responsible for oxidizing 5-mC to 5-hmC. TET enzymes belong to the broad family of Fe(II)/2-oxo-glutarate-dependent (2OGFE) oxygenases, which use 2-oxo-glutarate (2OG), as co-substrate, and ferrous ion (Fe(II)) as cofactor. After additional biochemical studies, it was discovered that these enzymes could oxidize 5-mC to generate oxidation products identified as 5-hmC, 5-formylcytosine (5-fC) and 5-carboxycytosine (5-caC). Finally, 5-caC is believed to be excised via the action of DNA glycosylases and replaced by the unmodified cytosine. The TET enzymes are very large proteins and hence it has been problematic to make these proteins in recombinant form and in sufficient quantities to use as a research reagent.

In order to identify the impact of the epigenome on phenotype, it is desirable to map the position of modified nucleotides and to understand when and where the various modifications arise. Sodium bisulfite sequencing is the predominant method for mapping modified cytosine in the genome. Unfortunately, this technique does not discriminate between 5-mC and 5-hmC. Different methods are required to distinguish 5-mC from 5-hmC and its oxidation products.

SUMMARY

Although *Neigleria gruberi* has not been previously reported to contain 5-mC or 5-hmC, the present inventors have surprisingly discovered that a protein from *N. gruberi* can be used in vitro to convert 5-mC to oxidized cytosines. That protein can be purified from natural sources or produced recombinantly, optionally as a fusion protein with another amino acid sequence to facilitate its purification or use.

Accordingly, in one aspect the invention provides a fusion protein in which a binding domain is fused to a recombinant 5-methylpyrimidine oxygenase (mYOX1) having a size less than 600 amino acids and having a catalytic domain having 90% or 100% identity with the amino acid sequence of SEQ ID NO:1. In certain embodiments, the mYOX1 has an amino acid sequence with at least 90% identity (or more, such as at least 91% identity, at least 92% identity, at least 93% identity, at least 94% identity, at least 95% identity, at least 96% identity, at least 97% identity, at least 98% identity, or at least 99% identity) to amino acids 209-296, 160-297, 154-304 or 1-321 of the amino acid sequence of SEQ ID NO:2 (mYOX1), and/or with the corresponding amino acids of any one of SEQ ID NOs:3-9 as aligned with SEQ ID NO:2 in FIG. 2B, optionally while retaining 90% or 100% identity with the amino acid sequence of SEQ ID NO:1. In other embodiments, the mYOX1 has an amino acid sequence with at least 90% identity (or more, such as at least 91% identity, at least 92% identity, at least 93% identity, at least 94% identity, at least 95% identity, at least 96% identity, at least 97% identity, at least 98% identity, or at least 99% identity) to the entire length of SEQ ID NO:2, 3, 4, 5, 6, 7, 8, or 9. The binding domain is capable of recognizing and binding to another molecule. Thus, in some embodiments the binding domain is a histidine tag ("His-tag"), a maltose-binding protein, a chitin-binding domain, or a DNA-binding domain, which may include a zinc finger and/or a transcription activator-like (TAL) effector domain. The fusion protein can be used as a mYOX1 (such as a 5-mC oxygenase or a thymine hydroxylase) in single- or double-stranded DNA or in RNA, typically at a pH of about 6 (generally between 5.5 and 6.5) to about 8, and, in some embodiments, at a pH of about 6 to about pH 7.5.

In another aspect, the invention provides buffered compositions containing a purified mYOX1 having a size less than 600 amino acids and having a catalytic domain having 90% or 100% identity with the amino acid sequence of SEQ ID NO:1. In certain embodiments, the mYOX1 has an amino acid sequence with at least 90% identity (or more, such as at least 91% identity, at least 92% identity, at least 93% identity, at least 94% identity, at least 95% identity, at least 96% identity, at least 97% identity, at least 98% identity, or at least 99% identity) to amino acids 209-296, 160-297, 154-304 or 1-321 of the amino acid sequence of SEQ ID NO:2, and/or with the corresponding amino acids of any one of SEQ ID NOs:3-9 as aligned with SEQ ID NO:2 in FIG. 2B, optionally while retaining 90% or 100% identity with the amino acid sequence of SEQ ID NO:1. In other embodiments, the mYOX1 has an amino acid sequence with at least 90% identity (or more, such as at least 91% identity, at least 92% identity, at least 93% identity, at least 94% identity, at least 95% identity, at least 96% identity, at least 97% identity, at least 98% identity, or at least 99% identity) to the entire length of SEQ ID NO:2, 3, 4, 5, 6, 7, 8, or 9. In various embodiments, the composition contains glycerol; and/or contains Fe(II), as cofactor, and α-ketoglutarate, as co-substrate, for the enzyme. In some of these embodiments, the composition does not contain ATP, which can interfere with subsequent oxidation of hydroxymethylated nucleotides; in other embodiments, the composition does contain ATP (e.g. to inhibit further oxidation). The composition is optionally at a pH from about 6 to about 8. In certain embodiments, the pH is about 6, or is from about 6 to about 7.5.

The buffered compositions can be used to generate a variety of oxidation products of 5-mC, including 5-hmC, 5-fC, and 5-caC. The distribution of oxidation products can be varied by varying the pH of the reaction buffer. Accordingly, in various embodiments the pH of the buffered composition is about 6; about 6.0 to about 6.5; about 6.0 to about 7.0; about 6.0 to about 7.5; about 6.0 to about 8.0; about 6.5 to about 7.0; about 6.5 to about 7.5; about 6.5 to about 8.0; about 7.0 to about 8.0; or about 7.5 to about 8.0.

In some embodiments, the buffered compositions also include a nucleic acid, such as single- or double-stranded DNA that may include 5-mC (as a substrate for the enzyme) and/or one or more of 5-hmC, 5-fC, or 5-caC (naturally-occurring, and/or resulting from the activity of the enzyme).

The invention also provides kits for modifying nucleic acids. The kits include a purified mYOX1 having a size less than 600 amino acids and having a catalytic domain having 90% or 100% identity with the amino acid sequence of SEQ ID NO:1, or any one of the buffered compositions or fusion proteins described above, together with a separate reaction buffer. In certain embodiments, the mYOX1 has an amino acid sequence with at least 90% identity (or more, such as at least 91% identity, at least 92% identity, at least 93% identity, at least 94% identity, at least 95% identity, at least 96% identity, at least 97% identity, at least 98% identity, or at least 99% identity) to amino acids 209-296, 160-297, 154-304 or 1-321 of the amino acid sequence of SEQ ID NO:2, optionally while retaining 90% or 100% identity with the amino acid sequence of SEQ ID NO:1. The reaction buffer has a pH typically from about 6 to about 8, and may contain contains Fe(II) and/or α-ketoglutarate. In various embodiments, the pH of the reaction buffer is about 6; about 6.0 to about 6.5; about 6.0 to about 7.0; about 6.0 to about 7.5; about 6.0 to about 8.0; about 6.5 to about 7.0; about 6.5 to about 7.5; about 6.5 to about 8.0; about 7.0 to about 8.0; or about 7.5 to about 8.0. The kit may also include a nucleic acid such as single- or double-stranded DNA that may include one or more 5-mC residues. Also, or alternatively, the kit may include: a reducing agent, such as sodium borohydride, or an additive, such as cobalt chloride; a β-glycosyltransferase (BGT) and UDP-glucose and/or UDP-glucosamine; a DNA glycosylase such as thymine DNA glycosylase; and/or an endonuclease, such as an endonuclease that cleaves DNA containing 5-hmC more efficiently than it cleaves DNA containing β-glucosyl-oxy-5-methyl-cytosine (5-ghmC) (e.g. AbaSI).

The invention also provides kits for detecting the 5-mC in double-stranded or single-stranded DNA or RNA by sequencing, e.g., single-molecular sequencing such as Pacific Biosciences platform. The kits include a purified mYOX1 having a size less than 600 amino acids and having a catalytic domain having 90% or 100% identity with the amino acid sequence of SEQ ID NO:1, or any one of the buffered compositions or fusion proteins described above, together with a separate reaction buffer. In certain embodiments, the mYOX1 has an amino acid sequence with at least 90% identity (or more, such as at least 91% identity, at least 92% identity, at least 93% identity, at least 94% identity, at least 95% identity, at least 96% identity, at least 97% identity, at least 98% identity, or at least 99% identity) to amino acids 209-296, 160-297, 154-304 or 1-321 of the amino acid sequence of SEQ ID NO:2, optionally while retaining 90% or 100% identity with the amino acid sequence of SEQ ID NO:1. The reaction buffer has a pH typically from about 6 to about 8, and may contain contains Fe(II) and/or α-ketoglutarate. In various embodiments, the pH of the reaction buffer is about 6; about 6.0 to about 6.5; about 6.0 to about 7.0; about 6.0 to about 7.5; about 6.0 to about 8.0; about 6.5 to about 7.0; about 6.5 to about 7.5; about 6.5 to about 8.0; about 7.0 to about 8.0; or about 7.5 to about 8.0. The kit may contain other DNA/RNA repair enzymes for the DNA or RNA to be used in the sequencing platforms.

In another aspect, the invention provides methods for differentiating a 5-mC from 5-hmC in a genome or genome fragment. In one embodiment, the method includes: reacting the isolated genome or genome fragment containing 5-mC and 5-hmC with UDP-glucose or UDP-glucosamine, a glycosyltransferase for transferring glucose or glucosamine to the 5-hmC, and one of the previously described fusion proteins or buffered compositions; cleaving the glucosylated template with a modification-dependent endonuclease that recognizes at least one of the modified nucleotides; and differentiating the 5-mC from the 5-hmC by an altered cleavage pattern. In another embodiment, the method includes: reacting the isolated genome or genome fragment containing 5-mC and 5-hmC with UDP-glucosamine and a glycosyltransferase for transferring glucosamine to the 5-hmC; subsequently reacting the isolated genome or genome fragment with one of the previously described fusion proteins or buffered compositions and optionally with a reducing agent; cleaving the template with a modification-dependent endonuclease that is capable of selectively cleaving a 5-hmC and not a 5-ghmC; and differentiating the 5-mC from one or more of its oxidation products by an altered cleavage pattern. In each of these embodiments, the modification-dependent endonuclease is optionally AbaSI.

The invention also provides methods of modifying a 5-mC oxygenase by introducing random or targeted mutations and changing the specificity of the enzyme so as to exclusively oxidize 5-mC to 5-hmC.

BRIEF DESCRIPTION OF THE FIGURES

FIG. 2A-B shows eight mYOX proteins in *Naegleria gruberi* and their alignments. This family of problems has a consensus sequence $(R/K)X_4HXDX_{12}GX_{18-30}DX_{10}HXVX_{7-72}RX_5FA$ (SEQ ID NO:1).

FIG. 2A shows the conserved domain structure of the 8 mYOX proteins anchored by the 2OGFE catalytic domain. An additional domain, a CHROMO domain, was detected in one of the proteins.

FIG. 2B shows multiple sequence alignment of the 2OGFE catalytic domain sequences in mYOX proteins. Alignment was performed by the PROMALS program (http://prodata.swmed.edu/promals/promals.php).

FIG. 4A shows the activity on double-stranded DNA with 24 fully-methylated CpG sites ("24× oligo"). FIG. 4B shows the activity on plasmid DNA ("pTXB1-M.SssI"). FIG. 4C shows the activity on genomic DNA ("IMR90").

All substrate DNA contained 5-mC. The generation of 5-hmC, 5-fC and 5-caC was monitored by liquid chromatography. The generation of 5-hmC was dependent on mYOX1, since no 5-hmC was detected in the absence of the enzyme. In addition, mYOX1 was able to convert thymine to 5-hmU, 5-fU and 5-caU (data not shown). These results indicate that mYOX1 is an active 5-mC oxygenase and thymine hydroxylase.

Figure 5:
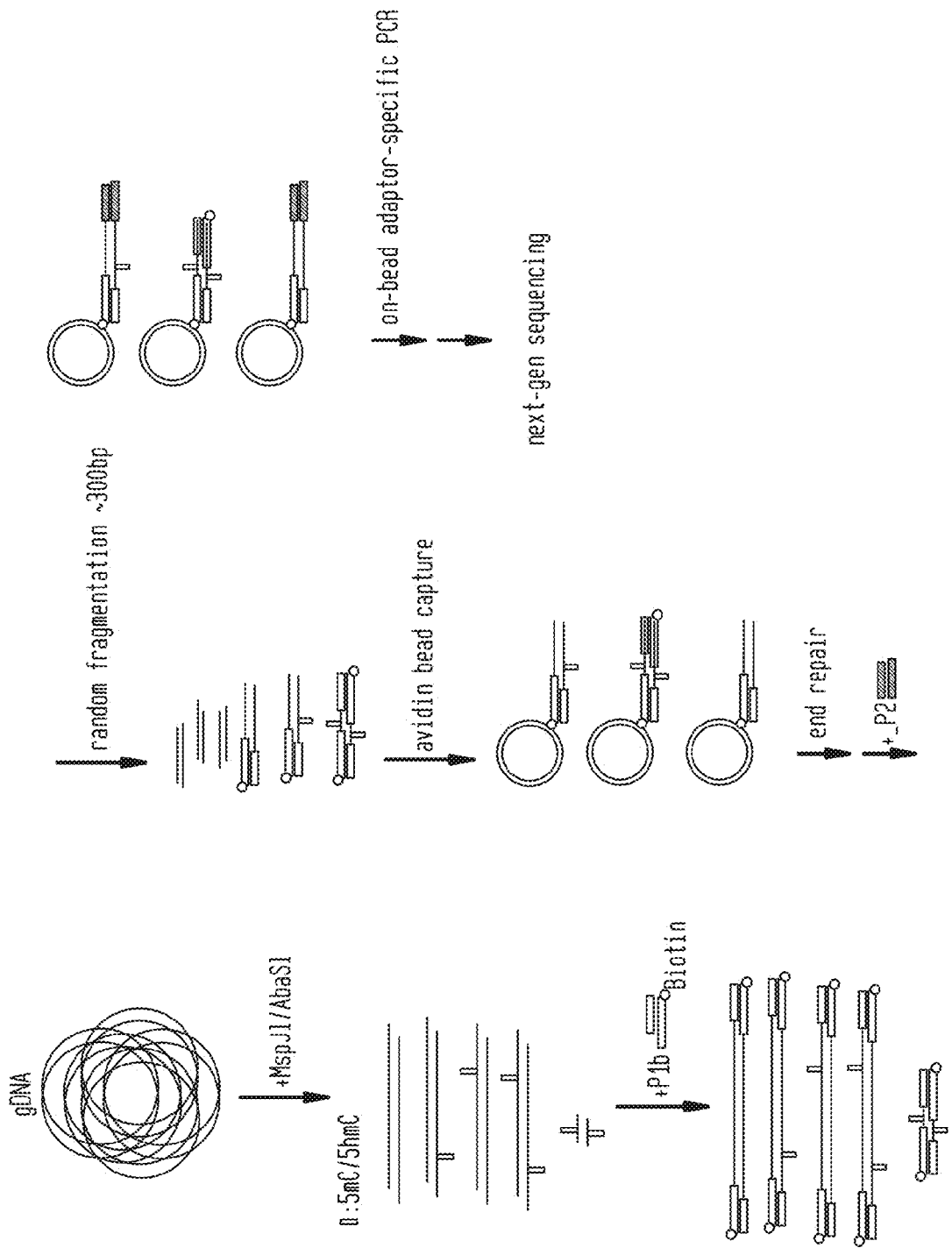

FIG. 5 shows methods for mapping methylome and hydroxymethylome using the DNA modification-dependent restriction endonucleases.

DETAILED DESCRIPTION OF EMBODIMENTS

Figure 1:
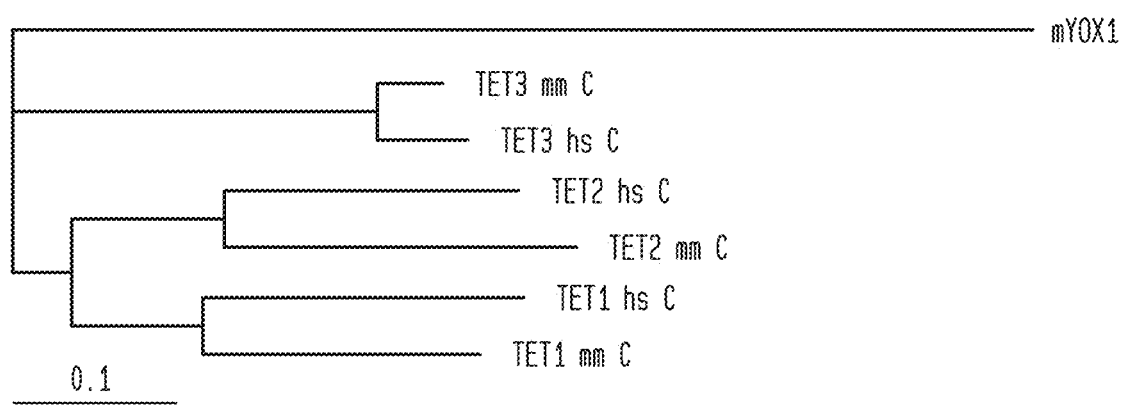
FIG. 1 shows a phylogram of mYOX1 in *Naegleria gruberi* and TET proteins based on the ClustalW multiple sequence alignment. TET1_hs_C, human TET1 truncated C-terminus; TET1_mm_C, mouse TET1 truncated C-terminus; TET2_hs_C, human TET2 truncated C-terminus; TET2_mm_C, mouse TET2 truncated C-terminus; TET3_hs_C, human TET3 truncated C-terminus; TET3_mm_C, mouse TET3 truncated C-terminus.

In general and in at least one aspect, a novel family of enzymes is described. Generally, these enzymes can be described as mYOXs, or, more specifically, 5-mC oxygenases that can use 2OG, as co-substrate, and ferrous ion (Fe(II)), as cofactor. This novel family, whose members are referred to in this application as mYOXs, is distantly related to the TET proteins, as shown in the phylogram of FIG. 1, sharing about 15% sequence identity with them. Compared to TET proteins, mYOXs have several advantages as reagents for oxygenating 5-mC. With sizes in the range of 174-583aa, mYOXs are substantially smaller than enzymes of the TET family (which are ~1600-2000aa), facilitating their recombinant production. Their small size renders these enzymes suitable as components in fusion proteins with, for example, DNA binding domains such as zinc fingers, and/or one or more additional enzymatic domains such as a glycosylase to promote the eventual excision of the modified cytosine. Moreover, in contrast to TET proteins, mYOXs operate more efficiently at pH 7.5 or less (e.g. at about pH 6), and do not require ATP which is significant because it reduces the possibility of side reactions, for example, phosphorylation, and permits use of the enzymes in conjunction with PCR amplification which is inhibited by ATP. An additional advantage of mYOX1 over TET proteins as research reagents includes its improved catalytic efficiency. For example, stoichiometrically fewer enzyme molecules are needed to oxidize 5-mCs when using mYOX1 rather than a TET enzyme.

One of the advantages of oxidizing 5-mC in vitro is the ability to add chemical or fluorescent labels onto DNA, which can be further coupled to sequencing technologies and map the DNA epigenomes.

mYOXs can be cloned and purified from *Naegleria gruberi*, a free-living single-cell protist as described in Example 1. Host cells suitable for expression include *E. coli*, yeast and insect cell systems producing greater than 10 µg/l, 20 µg/l, 30 µg/l, 50 µg/l, 70 µg/l, 100 µg/l, 200 µg/l, 300 µg/l, 400 µg/l, 500 µg/l and as much as 10 mg/liter of culture. A unit amount of mYOX1 is able to convert 1 pmol of 5-mC on DNA in 30 minutes at 34° C. in 1×mYOX1 reaction buffer at pH 6.0 (unit definition).

Exemplary mYOX protein sequences are provided in the following table:

| Name | Accession # | SEQ ID NO: | SEQUENCE |
|---|---|---|---|
| mYOX1 | XP_002667965.1 | 2 | MTTFKQQTIKEKETKRKYCIKGTTANLTQT HPNGPVCVNRGEEVANTTTLLDSGGGINK KSLLQNLLSKCKTTFQQSFTNANITLKDEK WLKNVRTAYFVCDHDGSVELAYLPNVLPK ELVEEFTEKFESIQTGRKKDTGYSGILDNS MPFNYVTADLSQELGQYLSEIVNPQINYYIS KLLTCVSSRTINYLVSLNDSYYALNNCLYPS TAFNSLKPSNDGHRIRKPHKDNLDITPSSL FYFGNFQNTEGYLELTDKNCKVFVQPGDVL FFKGNEYKHVVANITSGWRIGLVYFAHKG SKTKPYYEDTQKNSLKIHKETK |
| mYOX6 | XP_002674105.1 | 3 | MPMNYITSDLKTQLGEYLIGIVNPMLDETIT AALEILSPRTINYLTSLPHPYHILNNCIYPST AFNYLEPQIEKHRIKNAHKDTRDATPSVLF YLGDYDEKEGYLEFPEQNCKVFVKPGDLLL FKGNKYKHQVAPITSGTRLGLVYFAHKACK VMDFYDDYQKESLNKHKQQNQ |
| mYOX4 | XP_002676528.1 | 4 | MSINTTFNQKTTQSGEPPMMMRMTNSSTP PLTPKNCLPIFVYNDYGKLIREEQQQPTDII TNNNNSMMRSMPTTNRWETNPQTPLSVS PFQPLLPIPNFSHAFIVGNLPPSVSVRRKNR KMSEKPKNNSAPSKIMHQLELSVLNNQRR IAPKGPLADISNIQLPQQESTNKSNNTTPK KPRIRQLMLTTPLRESLQSNQSARSKYIDE EANNYSINDSPETTIIKTSNTKDSEHKAAM ATNLGLSTDDFECKPFETTTLPSVIDKNYLV VDKEGCTQLALLPNHIPTSVCKLIEVKCRK VSNLRHALKIQKASFYVNWWTKSQPMGY MCKDNESEIGKVVNEIAELLSDHCRNLLR MCNERVYKKISELKEDKFFAPCICFNILEHD LESRITKFHHDKMDYGVSVLFYFGDYSRG NLNVLDAGSSSTIVTRPGDAVILRGNYYKH SVQNIEPGNNKARYSIVFFAHSTHFLKKKY ELSPAAAKKAFLVDNPDFVSIKKRKQASSS SDVSVKKSKKSTEDNVEFIQTHTYLGNGY KSGHKNYQYYVKFNNSDQKEWKSYESLPK QAVASYWVKFKKLKSLSNQ |
| mYOX7 | XP_002668594.1 | 5 | MLEAQHHKLTIYTGMWGHMKPCVFIAADN CNKSGETIVENLLFKLGKIGSKLMEILSPFT MNFLSSLDPEIFLNHDLFPISATNFMIPGNK HRILKPHKDNQDVGLCIIFYFGNYNAPLEF VNKGSVFNTERGDVLLMRGSHFRHVVKPV DNGLLEHVHDPMRISVVLFAHKSLKMNPS YFLNAGSALKAHDEDFPEKAKKRKKKRK |

-continued

| Name | Accession # | SEQ ID NO: | SEQUENCE |
|---|---|---|---|
| mYOX8 | XP_002676954.1 | 6 | MFLRNILPENTTTEVTNILDKINQRRSKENY YIGSWGKSSSFLFKTNDTIFNELSSQFIKII NLLKNYVLEILKFGNNKMRKFLEKYNSSDF LSIYPTVCFNFLDKSVDENRILHIHPDKEDT GTSLIFYFGKFKGGAISFPELNFKLMVQSA DVLLFDGKNNLHAVESLHGKDDVRYSVVF FAHKADLGKTSYPMNRGEVMKGIKNKINN |
| mYOX5 | XP_002668409.1 | 7 | MDIGIDWRGTHFRHKNHLVKEEVCDRTN WIVLCPNGQVDIAFFPNAIPEELCLEMETV VANSDVDILSCKKAIIDGSWTRYGNGIYPV KTITTNQSILLHELNDKCGPFVLDKLKHINK NMFNKLDNINEDIKNYKIFAKYPTLALNVS HNENYNISKKPYRKHTDGNDIGLGVLTYFG SEIIEGGNLIIHIENLKVFNFPIQRRDLVFLN SKFYAHQVTKVTSGIRFGLVYFAGEAHFRV RNNDDFLPALPFNANDKELREERSKKGRK SMNEYKKRFLKKYLREKKKINKKRVKCKNK LK |
| mYOX2 | XP_002682154.1 | 8 | MGPLHVSQHDKKKPKHRRRKKQFLKAQAL TRVCWENEKSIDESGKTRVYKMIKEWEFL KGNNIQSNEPILSVYGVNDTIPKEISSNTII VTKEGMVEMALLKSVLPPSLLEECTQLCRE MSEWLATEKDIDKGSFFSGWWTMNMPM GYKCADSFRFELVDTKVKQIQALLHDTFQH ILELANPKLFAKLSKLTERGQTPVVCFNMIP TRNESVKEKFQGSYKSTDKVNRPKTNHRD RNDMGISAMFYMGKFGGGSLQLIRVNEHT PKTLVHIQAGDVVLLRANKYRHAVSPTRPQ SFPLANSSQTEVDDVKICENSSPTLNNPQA DDNTPTLINTCPKQEPTDGDNPVQSSKEP SNDYEQKRFSFIFFAHRSHFKHSKVYCGM GQRQALNAFKADHPYYQSQRMKKKLGDD CLDQSLILTEKRKPIKRNYALFNECGDDKQ EESDEEEYQQYEPKPTTEEYTIKVIVDHEKV FKGSDQSRKSYLYHIQWLGYPDETWEPYE HLDDCQVFEDYLKHHNISLFDEEEEDRKV DDSMLLPAWMHEDESLFEALLPIICCSTDN PRHHLDDVPPFDFNY |
| mYOX3 | XP_002668005.1 | 9 | MTEIVELSNIEPKDQKQAIIGGTWNRYGNS IEIVAGISDENNTLLDNLTNCCESFVLDKL WHLNRSMYNKLDTIEEKIKNFKTYAKYPSL ALNLLCKENYNGKVKPYRKHIDPNNNGMD VLMFFGKTFEGGNLIVSYHYTNIDFRMFTLP IQSGDLVFLNSRIYHHKVTKVTSGVRCGLV FFAGLDHFSVRKANYKKVKKEEYQKNMDD KLLALPFQQKDKDLRIERTKTGRKEIKQFH KNLQNNLPNKKRKK |

Figure 2A:
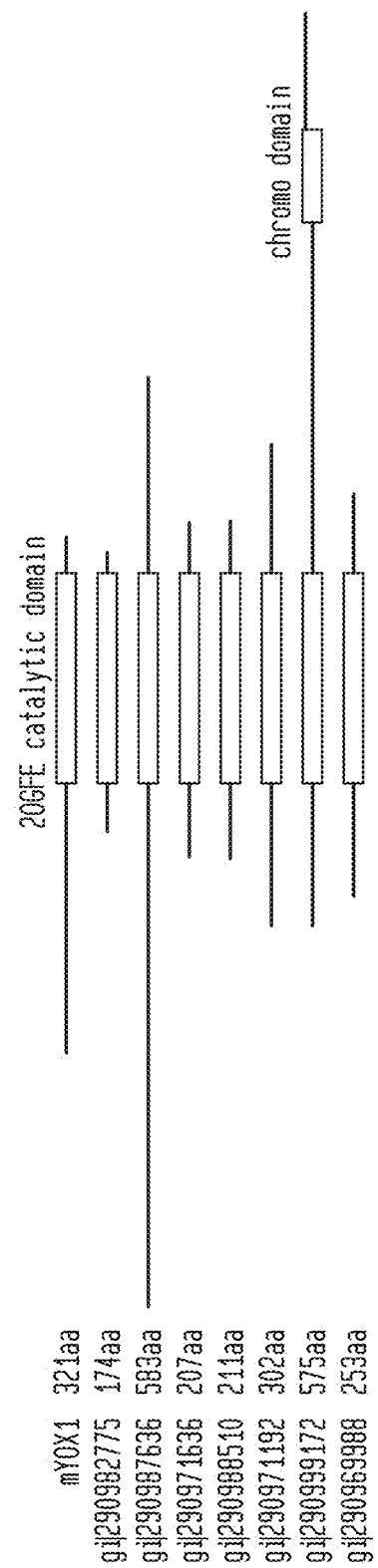
Figure 3:
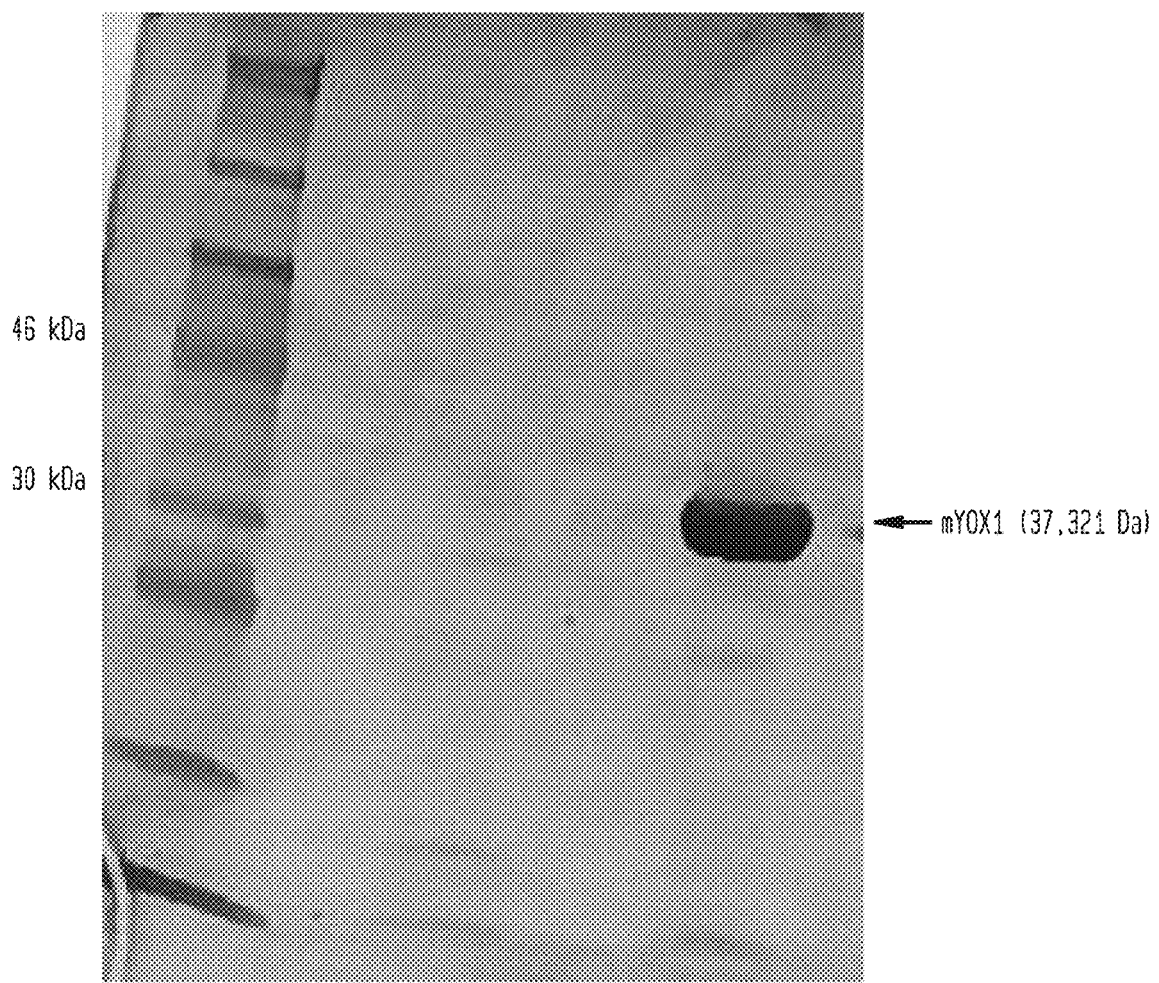
FIG. 3 shows a single band of purified recombinant mYOX1 having a molecular weight of 37,321 Dalton on an SDS-PAGE.

FIG. 2A-B depicts the common structure among these 8 mYOX proteins, including a conserved domain structure 9 (see panel A) and conserved sequences in that conserved domain as revealed by a multiple sequence alignment (see panel B). These 8 proteins share a common consensus sequence: $(R/K)X_4HXDX_{12}GX_{18-30}DX_{10}HXVX_{7-72}RX_5FA$ (SEQ ID NO:1).

Biochemical assays for characterization of these enzymes includes: non-quantitative assays, e.g., dot-blot assay using product-specific antibodies, thin-layer chromatography, and quantitative assays, e.g., LC/MS, radioactive assay etc.

mYOX enzymes may oxidize 5-mC through intermediate product forms to 5-caC. Mutants of these enzymes can be assayed for significant bias toward one oxidized form over another for example, a significant bias for conversion of 5-mC to 5-hmC or 5-mC to 5-fC or 5-caC. This allows direct detection of a single oxidation form and also a temporal means of tracking change in the oxidation state of modified nucleotides in the genome and correlation of these states and their changes to phenotypic change.

Additional mutants may include those that only oxidize 5-mC, or 5-hmC, or 5-fC, but not other modified forms of cytosine. For example, a mutant may oxidize 5-hmC to 5-fC or 5-caC, but will not work on 5-mC. These mutants may enable a variety of in vitro epigenomic mapping techniques.

Mutants can be engineered using standard techniques such as rational design by site-directed mutagenesis based on enzyme 3D structures and screening/selection methods in large random mutant libraries.

Embodiments of the invention include uses of mYOXs for mapping of both methylome and hydroxymethylome. For example, differentiation processes in eukaryotic organisms can be studied using *N. gruberi* as a model system. *N. gruberi* is a single-cell protist that can differentiate from an ameoba form to a flagella form in a synchronous manner. It thus forms a model system to study dynamic methylome/hydroxymethylome changes that contribute to the gene/pathway regulation during differentiation.

In one embodiment, the 5-mC in the genomic DNA can be converted to 5-hmC using an mYOX such as mYOX1 or other member of the mYOX family. Reducing agents, such as NaBH4, can be used in the reaction to ensure that any oxidation products in the form of 5-fC or 5-caC or naturally occurring instances of the same are converted to 5-hmC.

Any chemical or enzyme capable of promoting the reduction of 5-fC or 5-caC to 5-hmC can be used for that purpose. Many water-soluble metal or metalloid hydrides are able to reduce aldehydes and/or carboxylic acids to alcohols. Examples of such reducing agents are sodium borohydride and related compounds where from 1 to 3 of the hydrogens are replaced by other moieties, such as cyano and alkoxy containing up to about 5 carbon atoms. Examples of substituted borohydrides, all of which are sodium, potassium, or lithium salts, include cyanoborohydride, dicyanoborohydride, methoxyborohydride, dimethoxyborohydride, trimethoxyborohydride, ethoxyborohydride, diethoxyborohydride, triethoxyborohydride, propoxyborohydride, dipropoxyborohydride, tripropoxyborohydride, butoxyborohydride, dibutoxyborohydride, tributoxyborohydride, and so forth. Examples of other water-soluble metal hydrides include lithium borohydride, potassium borohydride, zinc borohydride, aluminum borohydride, zirconium borohydride, beryllium borohydride, and sodium bis(2-methoxyethoxy)aluminium hydride. Sodium borohydride can also be used in combination with a metal halide, such as cobalt(II), nickel(II), copper(II), zinc(II), cadmium (II), calcium (II), magnesium(II), aluminum(III), titanium (IV), hafnium(IV), or rhodium(III), each of which can be provided as a chloride, bromide, iodide, or fluoride salt. Alternatively, sodium borohydride can be used in combination with iodine, bromine, boron trifluoride diethyl etherate, trifluoroacetic acid, catechol-trifluoroacetic acid, sulfuric acid, or diglyme. Particular reducing strategies include the combination of potassium borohydride with lithium chloride, zinc chloride, magnesium chloride, or hafnium chloride; or the combination of lithium borohydride and chlorotrimethylsilane. Other reducing strategies include the use of borane, borane dimethyl sulfide complex, borane tetrahydrofuran complex, borane-ammonia complex, borane morpholine complex, borane dimethylamine complex, borane trimethylamine complex, borane N,N-diisopropylethylamine complex, borane pyridine complex, 2-picoline borane complex, borane 4-methylmorpholine complex, borane tert-butylamine complex, borane triphenylphosphine complex, borane N,N-diethylaniline complex, borane di(tert-butyl)phosphine complex, borane diphenylphosphine complex, borane ethylenediamine complex, or lithium ammonia borane. Alternative reducing strategies include the reduction of carboxylic acids via the formation of hydroxybenzotriazole esters, carboxy methyleniminium chlorides, carbonates, O-acylisoureas, acyl fluorides, cyanurates, mixed anhydrides, arylboronic anhydrides, acyl imidazolide, acyl azides, or N-acyl benzotriazoles, followed by reaction with sodium borohydride to give the corresponding alcohols.

Chemical groups, e.g., sugars such as glucose, can be added onto 5-hmC using a glycosyltransferase such as an α-glucosyltransferase (AGT) or a BGT. Useful glycosyltransferases can accept a nucleobase in a nucleic acid as a substrate. Exemplary BGT enzymes are found in bacteriophage, such as T4. The T4 BGT show little DNA sequence specificity, suggesting a mechanism of non-specific DNA binding combined with specific 5-hmC recognition.

Variants of the T4 BGT can be used. For example, the structure of T4 BGT and the identities of key residues in the enzyme are well understood, facilitating the construction of forms of the protein incorporating one or more amino acid deletions or substitutions. T4 BGT is a monomer comprising 351 amino acid residues and belongs to the α/β protein class. It is composed of two non-identical domains, both similar in topology to Rossmann nucleotide-binding folds, separated by a deep central cleft which forms the UDP-Glc binding site. Amino acids participating in the interaction with UDP include Ile238 (interactions with N3 and O4 of the base); Glu272 (interactions with O2' and O3' of the ribose); Ser189 (interacting with O11 of the α-phosphate); Arg191 (interacting with O12 of the α-phosphate); Arg269 (interacting with O6 of the α-phosphate and O22 of the β-phosphate); and Arg195 (interacting with O21 and O22 of the β-phosphate). Glu22 and Asp100 have been proposed to participate in the catalytic mechanism and other residues have been proposed to be involved in DNA binding or interactions with the UDP-associated sugar (Moréra et al. (1999) "T4 phage beta-glucosyltransferase: substrate binding and proposed catalytic mechanism." *J Mol. Biol.* 292(3):717-730, the entire disclosure of which is incorporated herein by reference).

Accordingly, a variant T4 BGT can be used to add a sugar to a nucleic acid. Variants optionally include an amino acid sequence at least 70% (e.g. at least 75%, at least 80%, at least 82%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%) identical to amino acids 1-351, 10-272 or 22-272 of T4 BGT. As assays for glycosylated nucleic acids (e.g. changes in susceptibility to cleavage by a glycosylation-sensitive endonuclease) are readily available, screening for variants retaining enzymatic activity is relatively straightforward.

Due to the more prominent difference between the 5-gmC and unmodified cytosine, direct observation of its signals in single-molecule sequencing experiments can be achieved using platforms such as PacBio (Pacific Biosciences, Menlo Park, Calif.) or Oxford Nanopore (Oxford, UK).

Modification-dependent or modification-sensitive endonucleases are described in WO2011/025819 incorporated by reference and also in REBASE® (www.neb.com, New England Biolabs, Ipswich, Mass.) and include for example, MspI, MfeI, Taq, and HpaII endonucleases. Optionally, the endonuclease preferentially binds to a hydroxymethylated cytosine or a glucosyl-oxy-methylated cytosine and cleave the bound nucleic acid at a defined distance from the recognition site. Exemplary endonucleases include those whose amino acid sequences are identical to, or are at least 95% identical to, an enzyme selected from the group consisting of PvuRts1I, PpeHI, EsaSS310P, EsaRBORFBP, PatTI, YkrI, EsaNI, SpeAI, BbiDI, PfrCORF1I80P, PcoORF314P, BmeDI, AbaSI, AbaCI, AbaAI, AbaUMB3ORFAP and Asp6ORFAP, as described in US Patent Application Publication No. 2012/0301881 and/or at least 95% identical to an enzyme referenced in Borgaro et al. (2013) "Characterization of the 5-hydroxymethylcytosine-specific DNA restriction endonucleases," *Nucleic Acids Research*, doi: 10.1093/nar/gkt102, the entire disclosures of each of which are incorporated herein by reference.

EXAMPLES

Example 1

Expression of mYOX1 mYOX1 was cloned in *E. coli*. T7 Express cells (New England Biolabs (NEB), Ipswich, Mass.) transformed with pTXB1-(His)6-mYOX1 which was induced with 50 μM IPTG at OD=0.8. The cells were grown at 16° C. for 12-16 hours and then lysed using a French press. The lysate supernatant was purified on a Ni-based affinity column followed by a heparin-based affinity column. The typical yield of isolated (His)6-mYOX1 was ~7-8 mg protein/L culture. The pure protein sample was stored in 20 mM TRIS, pH 7.5, 1 mM DTT, 500 mM NaCl, and 50% glycerol at −20° C.

Example 2

Determination of Activity of mYOX1

Figure 4A:
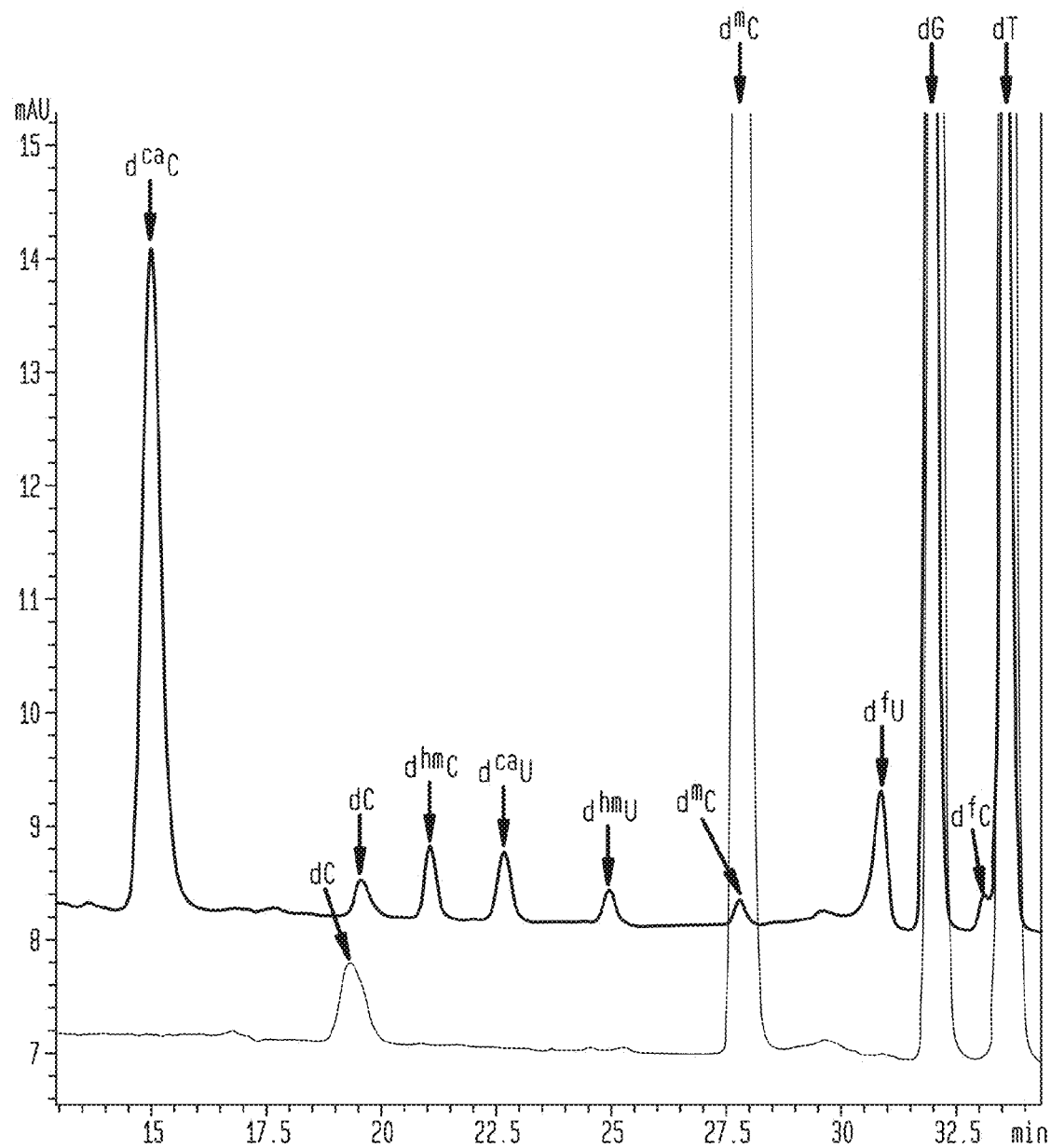
FIG. 4A-C shows the activity of mYOX1.

(A) Conversion of 5-mC in a double-stranded DNA oligomer with 24 fully-methylated CpG sites ("24× Oligo"), as reflected by the HPLC chromatogram shown in FIG. 4A. The DNA sequence of the top strand, with the methylation sites underlined, is: 5'-ATTACACGCGCGATATCGTTAA CGATAATTCGCGCGATTACGATCGATAACGCGTT AATA-3' (SEQ ID NO: 10). For each methylated cytosine in the top strand, the cytosine complementary to the subsequent guanine residue is also methylated, yielding a total of 24 methylated cytosines per double stranded DNA. The assay mix contained in a final volume of 20 μL: 50 mM Bis-TRIS pH 6.0, 50 mM NaCl, 1 mM dithiothreitol (DTT), 2 mM ascorbic acid, 2 mM α-ketoglutarate, 100 μM ferrous sulfate ($FeSO_4$), 2 μM oligonucleotide (24×), and 4 μM mYOX1.

The reaction mixture was incubated for 1 hour at 34° C. The protein was digested using proteinase K (NEB) at a final concentration of 1 μg/μL for 1 hour at 50° C. The DNA was recovered by using QIAquick® Nucleotide Removal Kit (QIAGEN, Valencia, Calif.). The recovered DNA was digested by a mixture of 0.5 U nuclease P1 (Sigma-Aldrich, St. Louis, Mo.), 5 U antarctic phosphatase (NEB), 2 U DNAse I (NEB) in 20 μL total volume for 1 hour at 37° C. The digested DNA was then subjected to LC-MS analysis. LC-MS was done on Agilent 1200 series (G1316A UV Detector, 6120 Mass Detector, Agilent, Santa Clara, Calif.) with Waters Atlantis T3 (4.6×150 mm, 3 μm, Waters, Milford, Mass.) column with in-line filter and guard. The results are shown in FIG. 4A, in which the blue profile depicts a reaction mixture without mYOX1 and the red profile depicts a reaction mixture with mYOX1. 5-mC peak is detected in the blue profile, 5-hmC, 5-fC and 5-caC peaks are detected in the red profile. The results of these experiments are summarized in the table below.

| DNA substrate | mYOX1 | $^{ca}C$ | $^{hm}C$ | $^{m}C$ | $^{f}C$ |
|---|---|---|---|---|---|
| 24× oligo | − | − | − | 100% | − |
| | + | 89.6% | 6.2% | 2.0% | 2.3% |
| pTXB1-M.Sss1 | − | − | − | 100% | − |
| | + | 91.2% | 1.8% | 1.0% | 5.9% |
| IMR90 | − | − | − | 100% | − |
| | + | 89.1% | 1.7% | 0.5% | 8.7% |

A variety of buffers and pHs were tested to assess the optimum buffer conditions for 5-mC conversion by mYOX1. The experiment was performed on a double-stranded DNA with one fully-methylated CpG site (5'-CGGCGTTTCCGGGTTCCATAGGCTCCGCCC CGGACTCTGATGACCAGGGCATCAC A-3'; underlined residue is 5-mC, as is the residue complementary to the adjacent guanine residue; SEQ ID NO: 11; "oligo 9"). The results are shown in the table below:

| Buffer | $^{ca}C$ | $^{hm}C$ | $^{m}C$ | $^{f}C$ |
|---|---|---|---|---|
| Citrate pH 5.0 | — | — | 100% | — |
| Citrate pH 5.5 | — | — | 100% | — |
| MES pH 5.5 | 10.2% | 40.9% | 9.2% | 39.7% |
| MES pH 5.75 | 7.7% | 42.4% | 7.0% | 43.0% |
| MES pH 6.0 | 25.1% | 20.8% | — | 54.1% |
| Bis-TRIS pH 6.0 | 38.5% | 15.7% | 2.1% | 43.6% |
| Bis-TRIS pH 6.5 | 26.1% | 19.0% | 0.9% | 54.0% |
| MOPS pH 6.5 | 38.8% | 13.6% | 2.1% | 45.4% |
| MOPS pH 6.75 | 41.7% | 10.0% | 0.7% | 47.5% |
| MOPS pH 7.0 | 31.7% | 18.8% | 0.6% | 48.9% |
| KH2PO4 pH7.0 | — | — | 100% | — |
| TRIS pH 7.5 | 5.9% | 56.8% | 7.1% | 30.1% |
| HEPES pH 7.3 | 20.5% | 22.2% | 1.0% | 56.4% |
| HEPES pH 7.5 | 18.5% | 37.4% | 1.2% | 42.8% |
| HEPES pH 8.0 | — | 16.8% | 81.2% | 2.0% |

As shown in the table, mYOX1 was active at pH 8.0, oxidizing a portion of the 5-mC to 5-hmC and 5-fC. However, the enzyme was even more active at lower pH. For example, at pH 7.5, approximately 90% of the 5-mC residues were oxidized, with most of the product present as 5-hmC and 5-fC. At pH 7.3, the proportions of 5-mC and 5-hmC decreased, with increasing proportions of 5-fC and 5-caC. The proportions of 5-mC and 5-hmC continued to decrease with decreasing pH through pH 6.0, at which point substantially all of the 5-mC nucleotides were oxidized more than one third to 5-caC. Thus, the enzyme appears to be maximally active at about pH 6. The pH conditions could be used to manipulate distribution of 5-mC oxidation products. The pH-dependence of mYOX1 activity was surprising, as TET enzymes are routinely used at pH 8.

The activity of mYOX1 was tested on single-stranded DNA (ssDNA) substrates and compared to that of a double-stranded DNA (dsDNA) with the same sequence under the same experimental conditions discussed for 24× oligo. Surprisingly, it was found that mYOX1 oxidizes 5-mC in ssDNA as efficiently as dsDNA. Substrates included double-stranded "oligo 9"; "hemi-oligo 9," a double stranded DNA identical to oligo 9 but lacking methylcytosine on the complementary strand; "ss oligo 9 (top)," a single stranded DNA including only the residues recited in SEQ ID NO: 11; and "ss oligo 9 (bottom)," a single stranded DNA including the residues complementary to the residues recited in SEQ ID NO:11.

| Substrate | $^{ca}C$ | $^{hm}C$ | $^{m}C$ | $^{f}C$ |
|---|---|---|---|---|
| ds oligo 9 | 80.8% | 6.9% | 1.7% | 10.6% |
| hemi-oligo 9 | 88.7% | 6.3% | 1.7% | 3.4% |
| ss oligo 9 (top) | 92.4% | 3.0% | 0.4% | 1.9% |
| ss oligo 9 (bottom) | 94.8 | 3.0% | 0.4% | 1.9% |

Interestingly, mYOX1 was further shown to exhibit activity on a 1.6 kb RNA substrate ("5-mc RNA") having all its cytosines in 5-mC form:

(SEQ ID NO: 12)
gggtctagaaataattttgtttaactttaagaaggagatatacatatgaa aatcgaagaaggtaaaggtcaccatcaccatcaccacggatccatggaag acgccaaaaacataaagaaaggcccggcgccattctatcctctagaggat ggaaccgctggagagcaactgcataaggctatgaagagatacgccctggt tcctggaacaattgcttttacagatgcacatatcgaggtgaacatcacgt acgcggaatacttcgaaatgtccgttcggttggcagaagctatgaaacga -continued

```
tatgggctgaatacaaatcacagaatcgtcgtatgcagtgaaaactctct
tcaattcttatgccggtgttgggcgcgttatttatcggagttgcagttg
cgcccgcgaacgacatttataatgaacgtgaattgctcaacagtatgaac
atttcgcagcctaccgtagtgtttgtttccaaaaaggggttgcaaaaaat
tttgaacgtgcaaaaaaattaccaataatccagaaaattattatcatgg
attctaaaacggattaccagggatttcagtcgatgtacacgttcgtcaca
tctcatctacctcccggttttaatgaatacgattttgtaccagagtcctt
tgatcgtgacaaaacaattgcactgataatgaattcctctggatctactg
ggttacctaagggtgtggcccttccgcatagaactgcctgcgtcagattc
tcgcatgccagagatcctattttggcaatcaaatcattccggatactgc
gattttaagtgttgttccattccatcacggttttggaatgtttactacac
tcggatatttgatatgtggatttcgagtcgtcttaatgtatagatttgaa
gaagagctgttttacgatcccttcaggattacaaaattcaaagtgcgtt
gctagtaccaaccctattttcattcttcgccaaaagcactctgattgaca
aatacgatttatctaatttacacgaaattgcttctggggcgcacctctt
tcgaaagaagtcggggaagcggttgcaaaacgcttccatcttccagggat
acgacaaggatatgggctcactgagactacatcagctattctgattacac
ccgaggggatgataaaccgggcgcggtcggtaaagttgttccattttt
gaagcgaaggttgtggatctggataccgggaaaacgctgggcgttaatca
gagaggcgaattatgtgtcagaggacctatgattatgtccggttatgtaa
acaatccggaagcgaccaacgccttgattgacaaggatggatggctacat
tctggagacatagcttactgggacgaagacgaacacttcttcatagttga
ccgcttgaagtctttaattaaatacaaaggatatcaggtggcccccgctg
aattggaatcgatattgttacaacaccccaacatcttcgacgcgggcgtg
gcaggtcttcccgacgatgacgccggtgaacttcccgccgccgttgttgt
tttggagcacggaaagacgatgacggaaaaagagatcgtggattacgtcg
ccagtcaagtaacaaccgcgaaaaagttgcgcggaggagttgtgtttgtg
gacgaagtaccgaaaggtcttaccggaaaactcgacgcaagaaaaatcag
agagatcctcataaaggccaagaagggcggaaagtccaaactcgagtaag
gttaacctgcaggagg.
```

The assay conditions were as follows: 50 mM Bis-TRIS pH 6.0, 50 mM NaCl, 1 mM DTT, 2 mM ascorbic acid, 2 mM α-ketoglutarate, 100 μM FeSO$_4$, 1 μg 5-mC RNA, and 4 μM mYOX1. The reaction mixture was incubated for 1 hour at 34° C. The protein was digested using proteinase K (NEB) at a final concentration of 1 μg/μL for 1 hour at 37° C. The RNA was recovered by using QIAquick® Nucleotide Removal Kit (QIAGEN, Valencia, Calif.). The recovered RNA was digested into nucleosides and analyzed by LC-MS as described in example 2A. The results were as follows:

| DNA substrate | mYOX1 | r$^{ca}$C | r$^{hm}$C | r$^m$C | r$^f$C |
|---|---|---|---|---|---|
| 5-mC RNA | – | – | – | 100% | – |
| | + | – | 40.9% | 36.8% | 22.3% |

Figure 4B:
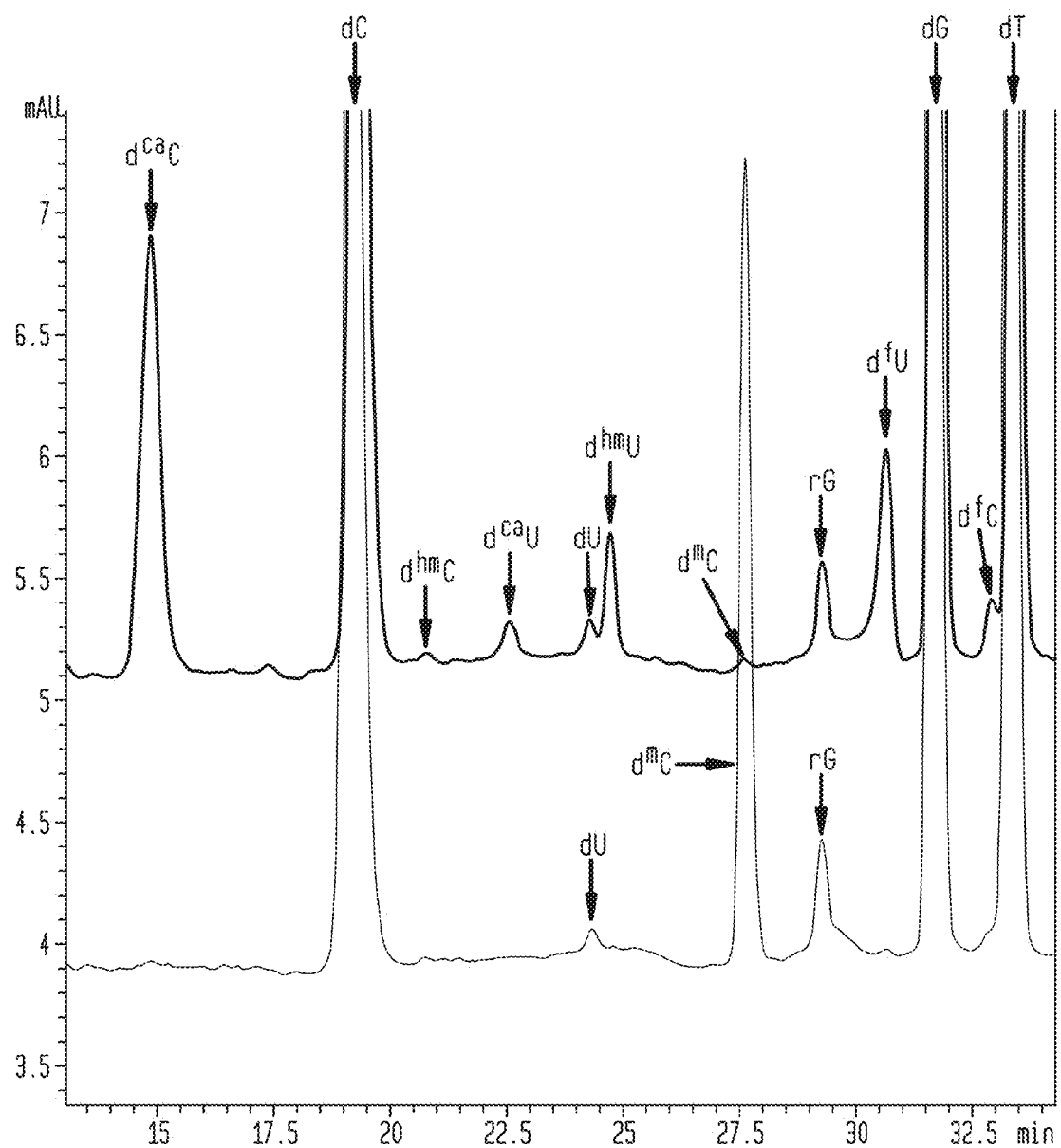
Figure 4C:
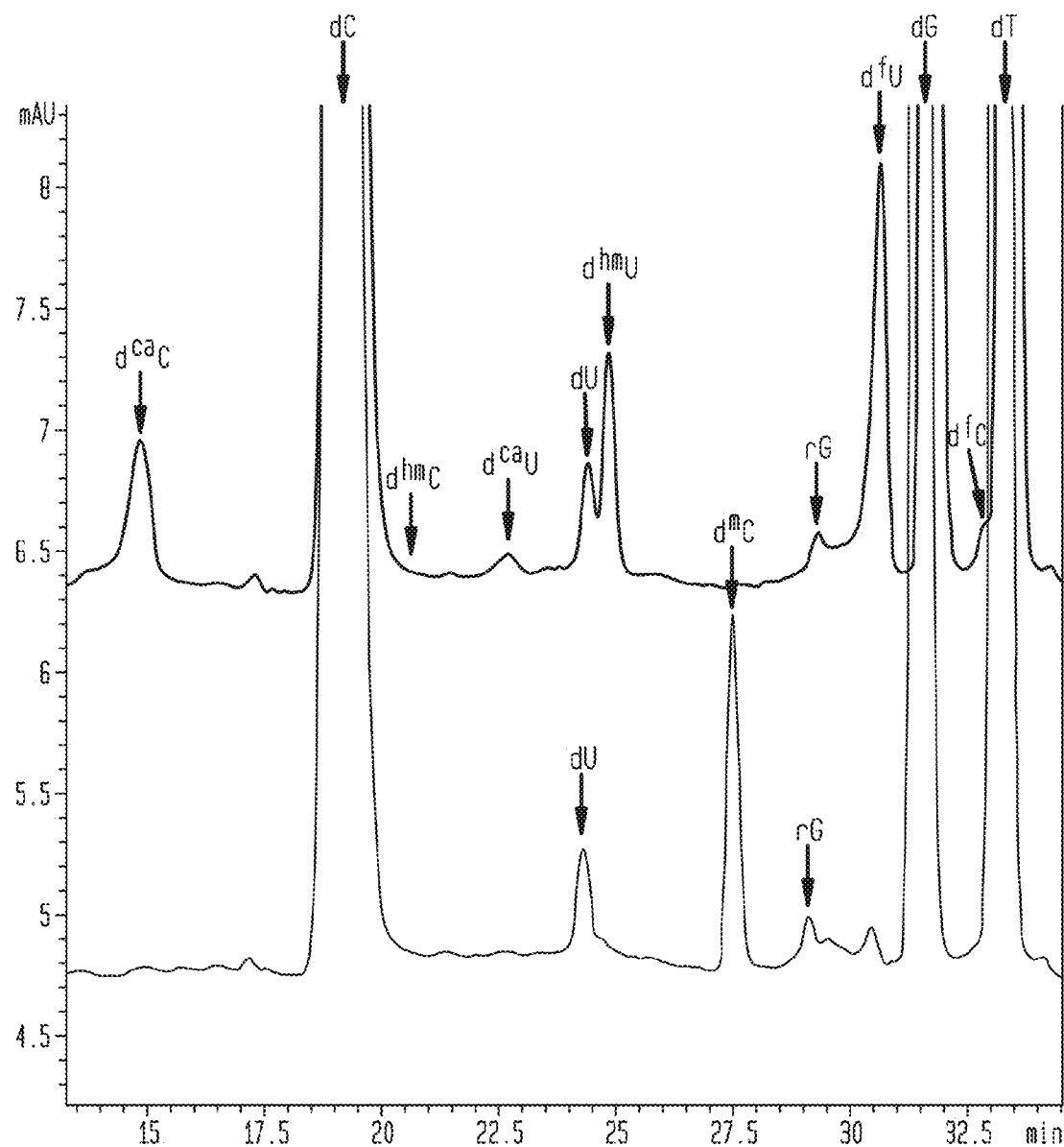

(B) Conversion of 5-mC in plasmid and genomic DNA, as depicted in the HPLC chromatogram shown in FIGS. 4B and 4C, respectively. The assay components are as follows: 50 mM Bis-TRIS pH 6.0, 50 mM NaCl, 1 mM DTT, 2 mM ascorbic acid, 2 mM α-ketoglutarate, 100 μM FeSO$_4$, 2 μg DNA, and 20 μM mYOX1.

The reaction mixture was incubated for 1 hour at 34° C. The reaction mixture was then digested with proteinase K for 1 hour at 50° C. The DNA was recovered by using QIAquick® PCR Purification Kit (QIAGEN, Valencia, Calif.). The recovered DNA was digested and analyzed by LC-MS as described in Example 2A. As shown, mYOX1 efficiently oxygenates 5-mC in plasmid and genomic DNA samples.

(C) ATP interferes with the chemical processivity of mYOX1 (ability to undergo second and third oxidation steps) as reflected in the table presented below. This is contradictory to what has been described for the TET enzymes where the presence of ATP has been required for the formation of higher amounts of 5-caC. Experimental conditions are as described before for oligos 24x and oligo9.

| DNA substrate | mYOX1 | 1 mM ATP | $^{ca}$C | $^{hm}$C | $^m$C | $^f$C |
|---|---|---|---|---|---|---|
| oligo9 | – | – | – | – | 100% | – |
| | + | – | 38.7% | 15.7% | 2.1% | 43.6% |
| | + | + | 13.6% | 40.9% | 2.3% | 43.2% |

Example 3 mYOX1 can be Used in Conjunction with BGT

An mYOX1/T4-BGT coupled assay was performed as described in Example 2A for genomic DNA (IMR90), with the following exceptions: 50 mM Hepes pH 7.0 was used instead of Bis-Tris pH 6.0, and 40 μM uridine diphosphoglucose (UDP-Glc) and 50 U T4 BGT were added in the oxidation reaction.

Alternatively, for bacterial genomic DNA (MG1655), the reaction was carried out exactly as described in Example 2A. Then the reaction mixture was digested with proteinase K for 1 hour at 50° C. The sample was then treated with 100 mM NaBH$_4$, 40 μM uridine diphosphoglucose (UDP-Glc) and 50 U T4-BGT in 1×NEBuffer 4 (NEB) and incubated for 1 hour at 37° C. The DNA was recovered by using QIAquick® PCR Purification Kit (QIAGEN, Valencia, Calif.). The recovered DNA was digested and analyzed by LC-MS as described in Example 2A, and the results are summarized in the table below.

| Substrate | T4-βGT | NaBH$_4$ | $^{ca}$C | $^{hm}$C | $^m$C | β-$^{ghm}$C | $^f$C |
|---|---|---|---|---|---|---|---|
| IMR90 | in oxidation reaction | – | 7.4% | – | 4.1% | 85.9% | 2.6% |
| MG1655 | after oxidation/ reduction | + | 29.3% | – | 3.0% | 67.7% | – |

The effects of increasing ATP concentration on the activity of mYOX1 when coupled with the activity of T4-BGT in the presence of NaBH$_4$ and UDP-Glc were tested. ATP concentrations higher than 1 mM exhibit inhibiting effects on the activity of mYOX1 to convert 5-mC to 5-hmC. The reaction was carried out exactly as described in Example 2A for oligo 9 except for the duration of the oxidation reaction (20 minutes instead of 1 hour), and the presence of varying amounts of ATP. The reaction mixture was then digested with proteinase K and glucosylated using T4 BGT as described above for MG1655 genomic DNA. The DNA was recovered by using QIAquick® PCR Purification Kit (QIAGEN, Valencia, Calif.). The recovered DNA was digested and analyzed by LC-MS as described in Example 2A, and the results are summarized in the table below.

| Substrate | ATP (mM) | $^{ca}C$ | $^{hm}C$ | $^mC$ | $\beta\text{-}^{ghm}C$ | $^fC$ |
|---|---|---|---|---|---|---|
| Oligo9 | 0.5 | 4.8% | — | 9.4% | 85.8% | — |
| | 1 | — | — | 13.4% | 83.7% | — |
| | 2 | — | — | 34.4% | 65.6% | — |
| | 4 | — | — | 62.1% | 37.9% | — |

Example 4

Qualitative and Quantitative Assays for Characterization of the mYOX Family of Enzymes Immunodot-blot assay: This is a qualitative, but relatively fast assay. Many samples can be tested simultaneously, which can be used for screening purposes, e.g., tracking active fractions during the enzyme purification process. By immobilizing the reacted DNA onto a membrane, it was possible to confirm the identity of the oxidation products of 5-mC, i.e. 5-hmC, 5-fC and 5-caC by probing with specific antibodies (obtainable from Active Motif, Carlsbad, Calif.).

LC-MS analysis: To quantify mYOX1 oxidation products, LC-MS analysis was performed on a reverse-phase Waters Atlantis T3 C18 column (3 μm, 4.6×150 mm) with an Agilent 1200 LC-MS system equipped with an Agilent G1315D DAD detector and an Agilent 6120 Quadruple MS detector. A binary solvent system with ammonium acetate (10 mM, pH 4.5) and methanol was used. The HPLC method included an isocratic condition with 2% methanol for 10 minutes followed by a slow gradient from 2% to 25% methanol in 30 minutes. The quantification of each nucleoside was based on the peak area by integration of each peak at 278 nm with UV detector. For more accurate quantification, each nucleoside peak can be quantified at its absorption maximum and adjusted by the extinction coefficient constant. The identity of each peak was confirmed by MS.

Example 5

5-hmC Specific Endonuclease Assay

We have developed a family of 5-hmC specific endonucleases which digest 5-hmC at the site of $^{5\text{-}hmC}N_{22\text{-}23}G$. By cloning the HpaII DNA methylase ($C^mCGG$) into a vector with only two CCGG sites, the vector will contain two sites of $^{5\text{-}mc}N_{22\text{-}23}G$. When the 5-mC in these sites were oxidized to 5-hmC, digestion using the 5-hmC specific endonuclease such as PvuRts1I or AbaSI produced a DNA fragment detectable in an agarose gel. This method detected 5-hmC only.

Example 6

Methods for Sequencing the Methylome and Hydroxymethylome Using the DNA Modification-Dependent Restriction Endonucleases Genomic DNA was digested with either MspJI or AbaSI. These enzymes cleaved the DNA at fixed distances from the modified cytosine leaving a sticky end (MspJI: 4-base 5'-overhang; AbaSI: 2-base 3'-overhang). The first biotinylated adaptor (P1b in FIG. 5) was then ligated to the cleaved ends. The ligated DNA was then subjected to random fragmentation to about 300 bp. Avidin beads were used to pull out the fragments with the ligated P1b. After polishing the ends, adaptor P2 was then ligated onto the DNA fragments on the beads. Adaptor-specific PCR was performed and the resultant DNA entered the library preparation pipeline for specific sequencing using the HiSeq® platform (Illumina, San Diego, Calif.). The end-sequencing was done from the P1 end.

Bioinformatic analysis of the sequencing reads utilized the P1 ends to mark the enzyme's cleavage sites. After mapping the read back to the reference genome, the modified cytosine was determined to be located at a fixed distance away from the cleavage sites and on either side.

What is claimed:

1. A method for differentiating a 5-methylcytosine (5-mC) from 5-hydroxymethylcytosine (5-hmC) in a genome or genome fragment, comprising:
 (a) reacting the isolated genome or genome fragment containing 5-mC and 5-hmC with:
  i. a UDP-associated sugar and a glucosyltransferase that transfers the sugar to the 5hmC, and
  ii. a polypeptide that has 5-methylpyrimidine oxygenase activity and comprises an amino acid sequence that is at least 90% identical to amino acids 154-304 of SEQ ID NO: 2;
 (b) cleaving the product of (a) with a modification-dependent endonuclease that recognizes at least one of the modified nucleotides; and
 (c) differentiating the 5-mC from the 5-hmC by an altered cleavage pattern.

2. The method of claim 1, wherein the modification-dependent endonuclease is AbaSI.

3. The method of claim 1, wherein the polypeptide comprises an amino acid sequence that is at least 95% identical to amino acids 154-304 of SEQ ID NO: 2.

4. The method of claim 1, wherein the polypeptide comprises an amino acid sequence that identical to amino acids 154-304 of SEQ ID NO: 2.

5. The method of claim 1, wherein the polypeptide comprises an amino acid sequence that is at least 90% identical to SEQ ID NO: 2.

6. The method of claim 1, wherein the polypeptide comprises an amino acid sequence that is at least 95% identical to SEQ ID NO: 2.

7. The method of claim 1, wherein the polypeptide comprises an amino acid sequence that is identical to SEQ ID NO: 2.

8. The method of claim 1, wherein the polypeptide further comprises a binding domain.

9. The method of claim 8, wherein the binding domain is selected from the group consisting of: a His-tag, a maltose-binding protein, a chitin binding domain, and a DNA binding domain.

10. The method of claim 8, wherein the binding domain comprising a zinc finger or transcription activator-like (TAL) effector domain.

11. The method of claim 1, wherein the polypeptide is a fusion protein.

12. The method of claim 1, wherein the reacting step (a) is done in a buffer that does not contain ATP.

13. The method of claim 1, wherein the reacting step (a) is done in a buffer that contains ATP.

14. The method of claim 1, wherein the reacting step (a) is done at a pH in the range of pH 6 to pH 8.

15. The method of claim 1, wherein the reacting step (a) is done at a pH in the range of pH 6 to pH 7.5.

16. The method of claim 1, wherein the reacting step (a) is done in a buffer that comprises Fe(II) and α-ketoglutarate.

17. The method of claim 1, wherein the UDP-associated sugar is UDP-glucose.

18. The method of claim 1, wherein the UDP-associated sugar is UDP-glucosamine.

19. The method of claim 1, wherein the glucosyltransferase is T4 DNA β-glucosyltransferase.

* * * * *

SEQUENCE LISTING

```
<160> NUMBER OF SEQ ID NOS: 12

<210> SEQ ID NO 1
<211> LENGTH: 146
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be either Arginine or Lysine
<220> FEATURE:
<221> NAME/KEY: MISC_FEATURE
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (9)..(20)
<223> OTHER INFORMATION: Xaa can be any naturally occurring amino acid
```

-continued

```
<220> FEATURE:
<221> NAME/KEY: MISC_FEATURE
<222> LOCATION: (22)..(52)
<223> OTHER INFORMATION: There can be 18-31 amino acids at this
      location. Xaa can be any naturally occurring amino acid
<220> FEATURE:
<221> NAME/KEY: MISC_FEATURE
<222> LOCATION: (54)..(63)
<223> OTHER INFORMATION: Xaa can be any naturally occurring amino acid
<220> FEATURE:
<221> NAME/KEY: MISC_FEATURE
<222> LOCATION: (65)..(65)
<223> OTHER INFORMATION: Xaa can be any naturally occurring amino acid
<220> FEATURE:
<221> NAME/KEY: MISC_FEATURE
<222> LOCATION: (67)..(138)
<223> OTHER INFORMATION: There can be 7-72 amino acids at this location.
      Xaa can be any naturally occurring amino acid
<220> FEATURE:
<221> NAME/KEY: MISC_FEATURE
<222> LOCATION: (140)..(144)
<223> OTHER INFORMATION: Xaa can be any naturally occurring amino acid

<400> SEQUENCE: 1

Xaa Xaa Xaa Xaa Xaa His Xaa Asp Xaa Xaa Xaa Xaa Xaa Xaa Xaa
 1               5                  10                  15

Xaa Xaa Xaa Xaa Gly Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Asp Xaa Xaa Xaa Xaa Xaa Xaa Xaa Xaa Xaa His
     50                  55                  60

Xaa Val Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Arg Xaa Xaa Xaa Xaa Xaa
    130                 135                 140

Phe Ala
145

<210> SEQ ID NO 2
<211> LENGTH: 321
<212> TYPE: PRT
<213> ORGANISM: Naegleria gruberi

<400> SEQUENCE: 2

Met Thr Thr Phe Lys Gln Gln Thr Ile Lys Glu Lys Glu Thr Lys Arg
 1               5                  10                  15

Lys Tyr Cys Ile Lys Gly Thr Thr Ala Asn Leu Thr Gln Thr His Pro
             20                  25                  30

Asn Gly Pro Val Cys Val Asn Arg Gly Glu Glu Val Ala Asn Thr Thr
         35                  40                  45

Thr Leu Leu Asp Ser Gly Gly Ile Asn Lys Lys Ser Leu Leu Gln
     50                  55                  60

Asn Leu Leu Ser Lys Cys Lys Thr Thr Phe Gln Gln Ser Phe Thr Asn
 65                  70                  75                  80
```

```
Ala Asn Ile Thr Leu Lys Asp Glu Lys Trp Leu Lys Asn Val Arg Thr
                85                  90                  95
Ala Tyr Phe Val Cys Asp His Asp Gly Ser Val Glu Leu Ala Tyr Leu
            100                 105                 110
Pro Asn Val Leu Pro Lys Glu Leu Val Glu Glu Phe Thr Glu Lys Phe
        115                 120                 125
Glu Ser Ile Gln Thr Gly Arg Lys Lys Asp Thr Gly Tyr Ser Gly Ile
    130                 135                 140
Leu Asp Asn Ser Met Pro Phe Asn Tyr Val Thr Ala Asp Leu Ser Gln
145                 150                 155                 160
Glu Leu Gly Gln Tyr Leu Ser Glu Ile Val Asn Pro Gln Ile Asn Tyr
                165                 170                 175
Tyr Ile Ser Lys Leu Leu Thr Cys Val Ser Ser Arg Thr Ile Asn Tyr
            180                 185                 190
Leu Val Ser Leu Asn Asp Ser Tyr Ala Leu Asn Asn Cys Leu Tyr
        195                 200                 205
Pro Ser Thr Ala Phe Asn Ser Leu Lys Pro Ser Asn Asp Gly His Arg
    210                 215                 220
Ile Arg Lys Pro His Lys Asp Asn Leu Asp Ile Thr Pro Ser Ser Leu
225                 230                 235                 240
Phe Tyr Phe Gly Asn Phe Gln Asn Thr Glu Gly Tyr Leu Glu Leu Thr
                245                 250                 255
Asp Lys Asn Cys Lys Val Phe Val Gln Pro Gly Asp Val Leu Phe Phe
            260                 265                 270
Lys Gly Asn Glu Tyr Lys His Val Val Ala Asn Ile Thr Ser Gly Trp
        275                 280                 285
Arg Ile Gly Leu Val Tyr Phe Ala His Lys Gly Ser Lys Thr Lys Pro
    290                 295                 300
Tyr Tyr Glu Asp Thr Gln Lys Asn Ser Leu Lys Ile His Lys Glu Thr
305                 310                 315                 320
Lys

<210> SEQ ID NO 3
<211> LENGTH: 174
<212> TYPE: PRT
<213> ORGANISM: Naegleria gruberi

<400> SEQUENCE: 3

Met Pro Met Asn Tyr Ile Thr Ser Asp Leu Lys Thr Gln Leu Gly Glu
1               5                   10                  15
Tyr Leu Ile Gly Ile Val Asn Pro Met Leu Asp Glu Thr Ile Thr Ala
            20                  25                  30
Ala Leu Glu Ile Leu Ser Pro Arg Thr Ile Asn Tyr Leu Thr Ser Leu
        35                  40                  45
Pro His Pro Tyr His Ile Leu Asn Asn Cys Ile Tyr Pro Ser Thr Ala
    50                  55                  60
Phe Asn Tyr Leu Glu Pro Gln Ile Glu Lys His Arg Ile Lys Asn Ala
65                  70                  75                  80
His Lys Asp Thr Arg Asp Ala Thr Pro Ser Val Leu Phe Tyr Leu Gly
                85                  90                  95
Asp Tyr Asp Glu Lys Glu Gly Tyr Leu Glu Phe Pro Glu Gln Asn Cys
            100                 105                 110
Lys Val Phe Val Lys Pro Gly Asp Leu Leu Leu Phe Lys Gly Asn Lys
        115                 120                 125
```

Tyr Lys His Gln Val Ala Pro Ile Thr Ser Gly Thr Arg Leu Gly Leu
    130                 135                 140

Val Tyr Phe Ala His Lys Ala Cys Lys Val Met Asp Phe Tyr Asp Asp
145                 150                 155                 160

Tyr Gln Lys Glu Ser Leu Asn Lys His Lys Gln Gln Asn Gln
                165                 170

<210> SEQ ID NO 4
<211> LENGTH: 583
<212> TYPE: PRT
<213> ORGANISM: Naegleria gruberi

<400> SEQUENCE: 4

Met Ser Ile Asn Thr Thr Phe Asn Gln Lys Thr Thr Gln Ser Gly Glu
1               5                   10                  15

Pro Pro Met Met Met Arg Met Thr Asn Ser Ser Thr Pro Pro Leu Thr
                20                  25                  30

Pro Lys Asn Cys Leu Pro Ile Phe Val Tyr Asn Asp Tyr Gly Lys Leu
            35                  40                  45

Ile Arg Glu Gln Gln Gln Pro Thr Asp Ile Ile Thr Asn Asn Asn
    50                  55                  60

Asn Ser Met Met Arg Ser Met Pro Thr Thr Asn Arg Trp Glu Thr Asn
65                  70                  75                  80

Pro Gln Thr Pro Leu Ser Val Ser Pro Phe Gln Pro Leu Leu Pro Ile
                85                  90                  95

Pro Asn Phe Ser His Ala Phe Ile Val Gly Asn Leu Pro Pro Ser Val
            100                 105                 110

Ser Val Arg Arg Lys Asn Arg Lys Met Ser Glu Lys Pro Lys Asn Asn
        115                 120                 125

Ser Ala Pro Ser Lys Ile Met His Gln Leu Glu Leu Ser Val Leu Asn
    130                 135                 140

Asn Gln Arg Arg Ile Ala Pro Lys Gly Pro Leu Ala Asp Ile Ser Asn
145                 150                 155                 160

Ile Gln Leu Pro Gln Gln Glu Ser Thr Asn Lys Ser Asn Asn Thr Thr
                165                 170                 175

Pro Lys Lys Pro Arg Ile Arg Gln Leu Met Leu Thr Thr Pro Leu Arg
            180                 185                 190

Glu Ser Leu Gln Ser Asn Gln Ser Ala Arg Ser Lys Tyr Ile Asp Glu
        195                 200                 205

Glu Ala Asn Asn Tyr Ser Ile Asn Asp Ser Pro Glu Thr Thr Ile Ile
    210                 215                 220

Lys Thr Ser Asn Thr Lys Asp Ser Glu His Lys Ala Ala Met Ala Thr
225                 230                 235                 240

Asn Leu Gly Leu Ser Thr Asp Asp Phe Glu Cys Lys Pro Phe Glu Thr
                245                 250                 255

Thr Thr Leu Pro Ser Val Ile Asp Lys Asn Tyr Leu Val Val Asp Lys
            260                 265                 270

Glu Gly Cys Thr Gln Leu Ala Leu Leu Pro Asn His Ile Pro Thr Ser
        275                 280                 285

Val Cys Lys Leu Ile Glu Val Lys Cys Arg Lys Val Ser Asn Leu Arg
    290                 295                 300

His Ala Leu Lys Ile Gln Lys Ala Ser Phe Tyr Val Asn Trp Trp Thr
305                 310                 315                 320

Lys Ser Gln Pro Met Gly Tyr Met Cys Lys Asp Asn Glu Ser Glu Ile
                325                 330                 335

```
Gly Lys Val Val Asn Glu Ile Ala Glu Leu Leu Ser Asp His Cys Arg
            340                 345                 350

Asn Leu Leu Arg Met Cys Asn Glu Arg Val Tyr Lys Lys Ile Ser Glu
        355                 360                 365

Leu Lys Glu Asp Lys Phe Phe Ala Pro Cys Ile Cys Phe Asn Ile Leu
    370                 375                 380

Glu His Asp Leu Glu Ser Arg Ile Thr Lys Phe His Asp Lys Met
385                 390                 395                 400

Asp Tyr Gly Val Ser Val Leu Phe Tyr Phe Gly Asp Tyr Ser Arg Gly
                    405                 410                 415

Asn Leu Asn Val Leu Asp Ala Gly Ser Ser Ser Thr Ile Val Thr Arg
                420                 425                 430

Pro Gly Asp Ala Val Ile Leu Arg Gly Asn Tyr Tyr Lys His Ser Val
            435                 440                 445

Gln Asn Ile Glu Pro Gly Asn Asn Lys Ala Arg Tyr Ser Ile Val Phe
        450                 455                 460

Phe Ala His Ser Thr His Phe Leu Lys Lys Lys Tyr Glu Leu Ser Pro
465                 470                 475                 480

Ala Ala Ala Lys Lys Ala Phe Leu Val Asp Asn Pro Asp Phe Val Ser
                485                 490                 495

Ile Lys Lys Arg Lys Gln Ala Ser Ser Ser Asp Val Ser Val Lys
            500                 505                 510

Lys Ser Lys Lys Ser Thr Glu Asp Asn Val Glu Phe Ile Gln Thr His
        515                 520                 525

Thr Tyr Leu Gly Asn Gly Tyr Lys Ser Gly His Lys Asn Tyr Gln Tyr
    530                 535                 540

Tyr Val Lys Phe Asn Asn Ser Asp Gln Lys Glu Trp Lys Ser Tyr Glu
545                 550                 555                 560

Ser Leu Pro Lys Gln Ala Val Ala Ser Tyr Trp Val Lys Phe Lys Lys
                565                 570                 575

Leu Lys Ser Leu Ser Asn Gln
            580

<210> SEQ ID NO 5
<211> LENGTH: 207
<212> TYPE: PRT
<213> ORGANISM: Naegleria gruberi

<400> SEQUENCE: 5

Met Leu Glu Ala Gln His His Lys Leu Thr Ile Tyr Thr Gly Met Trp
1               5                   10                  15

Gly His Met Lys Pro Cys Val Phe Ile Ala Ala Asp Asn Cys Asn Lys
            20                  25                  30

Ser Gly Glu Thr Ile Val Glu Asn Leu Leu Phe Lys Leu Gly Lys Ile
        35                  40                  45

Gly Ser Lys Leu Met Glu Ile Leu Ser Pro Phe Thr Met Asn Phe Leu
    50                  55                  60

Ser Ser Leu Asp Pro Glu Ile Phe Leu Asn His Asp Leu Phe Pro Ile
65                  70                  75                  80

Ser Ala Thr Asn Phe Met Ile Pro Gly Asn Lys His Arg Ile Leu Lys
                85                  90                  95

Pro His Lys Asp Asn Gln Asp Val Gly Leu Cys Ile Ile Phe Tyr Phe
            100                 105                 110

Gly Asn Tyr Asn Ala Pro Leu Glu Phe Val Asn Lys Gly Ser Val Phe
        115                 120                 125
```

```
Asn Thr Glu Arg Gly Asp Val Leu Leu Met Arg Gly Ser His Phe Arg
    130                 135                 140

His Val Val Lys Pro Val Asp Asn Gly Leu Leu Glu His Val His Asp
145                 150                 155                 160

Pro Met Arg Ile Ser Val Val Leu Phe Ala His Lys Ser Leu Lys Met
                165                 170                 175

Asn Pro Ser Tyr Phe Leu Asn Ala Gly Ser Ala Leu Lys Ala His Asp
            180                 185                 190

Glu Asp Phe Pro Glu Lys Ala Lys Lys Arg Lys Lys Arg Lys
        195                 200                 205
```

<210> SEQ ID NO 6
<211> LENGTH: 211
<212> TYPE: PRT
<213> ORGANISM: Naegleria gruberi

<400> SEQUENCE: 6

```
Met Phe Leu Arg Asn Ile Leu Pro Glu Asn Thr Thr Glu Val Thr
1               5                   10                  15

Asn Ile Leu Asp Lys Ile Asn Gln Arg Arg Ser Lys Glu Asn Tyr Tyr
                20                  25                  30

Ile Gly Ser Trp Gly Lys Ser Ser Phe Leu Phe Lys Thr Asn Asp
            35                  40                  45

Thr Ile Phe Asn Glu Leu Ser Ser Gln Phe Ile Lys Ile Ile Asn Leu
    50                  55                  60

Leu Lys Asn Tyr Val Leu Glu Ile Leu Lys Phe Gly Asn Asn Lys Met
65                  70                  75                  80

Arg Lys Phe Leu Glu Lys Tyr Asn Ser Ser Asp Phe Leu Ser Ile Tyr
                85                  90                  95

Pro Thr Val Cys Phe Asn Phe Leu Asp Lys Ser Val Asp Glu Asn Arg
                100                 105                 110

Ile Leu His Ile His Pro Asp Lys Glu Asp Thr Gly Thr Ser Leu Ile
            115                 120                 125

Phe Tyr Phe Gly Lys Phe Lys Gly Gly Ala Ile Ser Phe Pro Glu Leu
    130                 135                 140

Asn Phe Lys Leu Met Val Gln Ser Ala Asp Val Leu Leu Phe Asp Gly
145                 150                 155                 160

Lys Asn Asn Leu His Ala Val Glu Ser Leu His Gly Lys Asp Asp Val
                165                 170                 175

Arg Tyr Ser Val Val Phe Phe Ala His Lys Ala Asp Leu Gly Lys Thr
                180                 185                 190

Ser Tyr Pro Met Asn Arg Gly Glu Val Met Lys Gly Ile Lys Asn Lys
            195                 200                 205

Ile Asn Asn
    210
```

<210> SEQ ID NO 7
<211> LENGTH: 302
<212> TYPE: PRT
<213> ORGANISM: Naegleria gruberi

<400> SEQUENCE: 7

```
Met Asp Ile Gly Ile Asp Trp Arg Gly Thr His Phe Arg His Lys Asn
1               5                   10                  15

His Leu Val Lys Glu Glu Val Cys Asp Arg Thr Asn Trp Ile Val Leu
                20                  25                  30
```

```
Cys Pro Asn Gly Gln Val Asp Ile Ala Phe Phe Pro Asn Ala Ile Pro
         35                  40                  45

Glu Glu Leu Cys Leu Glu Met Glu Thr Val Val Ala Asn Ser Asp Val
 50                  55                  60

Asp Ile Leu Ser Cys Lys Lys Ala Ile Ile Asp Gly Ser Trp Thr Arg
 65                  70                  75                  80

Tyr Gly Asn Gly Ile Tyr Pro Val Lys Thr Ile Thr Asn Gln Ser
                 85                  90                  95

Ile Leu Leu His Glu Leu Asn Asp Lys Cys Gly Pro Phe Val Leu Asp
                100                 105                 110

Lys Leu Lys His Ile Asn Lys Asn Met Phe Asn Lys Leu Asp Asn Ile
                115                 120                 125

Asn Glu Asp Ile Lys Asn Tyr Lys Ile Phe Ala Lys Tyr Pro Thr Leu
130                 135                 140

Ala Leu Asn Val Ser His Asn Glu Asn Tyr Asn Ile Ser Lys Lys Pro
145                 150                 155                 160

Tyr Arg Lys His Thr Asp Gly Asn Asp Ile Gly Leu Gly Val Leu Thr
                165                 170                 175

Tyr Phe Gly Ser Glu Ile Ile Glu Gly Gly Asn Leu Ile Ile His Ile
                180                 185                 190

Glu Asn Leu Lys Val Phe Asn Phe Pro Ile Gln Arg Arg Asp Leu Val
                195                 200                 205

Phe Leu Asn Ser Lys Phe Tyr Ala His Gln Val Thr Lys Val Thr Ser
        210                 215                 220

Gly Ile Arg Phe Gly Leu Val Tyr Phe Ala Gly Glu Ala His Phe Arg
225                 230                 235                 240

Val Arg Asn Asn Asp Asp Phe Leu Pro Ala Leu Pro Phe Asn Ala Asn
                245                 250                 255

Asp Lys Glu Leu Arg Glu Glu Arg Ser Lys Lys Gly Arg Lys Ser Met
                260                 265                 270

Asn Glu Tyr Lys Lys Arg Phe Leu Lys Lys Tyr Leu Arg Glu Lys Lys
            275                 280                 285

Lys Ile Asn Lys Lys Arg Val Lys Cys Lys Asn Lys Leu Lys
        290                 295                 300

<210> SEQ ID NO 8
<211> LENGTH: 575
<212> TYPE: PRT
<213> ORGANISM: Naegleria gruberi

<400> SEQUENCE: 8

Met Gly Pro Leu His Val Ser Gln His Asp Lys Lys Pro Lys His
1               5                   10                  15

Arg Arg Arg Lys Lys Gln Phe Leu Lys Ala Gln Ala Leu Thr Arg Val
                20                  25                  30

Cys Trp Glu Asn Glu Lys Ser Ile Asp Glu Ser Gly Lys Thr Arg Val
        35                  40                  45

Tyr Lys Met Ile Lys Glu Trp Glu Phe Leu Lys Gly Asn Asn Ile Gln
 50                  55                  60

Ser Asn Glu Pro Ile Leu Ser Val Tyr Gly Val Asn Asp Thr Ile Pro
 65                  70                  75                  80

Lys Glu Ile Ser Ser Asn Thr Ile Ile Val Thr Lys Glu Gly Met Val
                85                  90                  95

Glu Met Ala Leu Leu Lys Ser Val Leu Pro Pro Ser Leu Leu Glu Glu
                100                 105                 110
```

```
Cys Thr Gln Leu Cys Arg Glu Met Ser Glu Trp Leu Ala Thr Glu Lys
            115                 120                 125

Asp Ile Asp Lys Gly Ser Phe Phe Ser Gly Trp Trp Thr Met Asn Met
        130                 135                 140

Pro Met Gly Tyr Lys Cys Ala Asp Ser Phe Arg Phe Glu Leu Val Asp
145                 150                 155                 160

Thr Lys Val Lys Gln Ile Gln Ala Leu Leu His Asp Thr Phe Gln His
                165                 170                 175

Ile Leu Glu Leu Ala Asn Pro Lys Leu Phe Ala Lys Leu Ser Lys Leu
            180                 185                 190

Thr Glu Arg Gly Gln Thr Pro Val Val Cys Phe Asn Met Ile Pro Thr
        195                 200                 205

Arg Asn Glu Ser Val Lys Glu Lys Phe Gln Gly Ser Tyr Lys Ser Thr
210                 215                 220

Asp Lys Val Asn Arg Pro Lys Thr Asn His Arg Asp Arg Asn Asp Met
225                 230                 235                 240

Gly Ile Ser Ala Met Phe Tyr Met Gly Lys Phe Gly Gly Gly Ser Leu
                245                 250                 255

Gln Leu Ile Arg Val Asn Glu His Thr Pro Lys Thr Leu Val His Ile
            260                 265                 270

Gln Ala Gly Asp Val Val Leu Leu Arg Ala Asn Lys Tyr Arg His Ala
        275                 280                 285

Val Ser Pro Thr Arg Pro Gln Ser Phe Pro Leu Ala Asn Ser Ser Gln
290                 295                 300

Thr Glu Val Asp Asp Val Lys Ile Cys Glu Asn Ser Ser Pro Thr Leu
305                 310                 315                 320

Asn Asn Pro Gln Ala Asp Asp Asn Thr Pro Thr Leu Ile Asn Thr Cys
                325                 330                 335

Pro Lys Gln Glu Pro Thr Asp Gly Asp Asn Pro Val Gln Ser Ser Lys
            340                 345                 350

Glu Pro Ser Asn Asp Tyr Glu Gln Lys Arg Phe Ser Phe Ile Phe Phe
        355                 360                 365

Ala His Arg Ser His Phe Lys His Ser Lys Val Tyr Cys Gly Met Gly
370                 375                 380

Gln Arg Gln Ala Leu Asn Ala Phe Lys Ala Asp His Pro Tyr Tyr Gln
385                 390                 395                 400

Ser Gln Arg Met Lys Lys Leu Gly Asp Asp Cys Leu Asp Gln Ser
                405                 410                 415

Leu Ile Leu Thr Glu Lys Arg Lys Pro Ile Lys Arg Asn Tyr Ala Leu
            420                 425                 430

Phe Asn Glu Cys Gly Asp Asp Lys Gln Glu Glu Ser Asp Glu Glu
        435                 440                 445

Tyr Gln Gln Tyr Glu Pro Lys Pro Thr Thr Glu Glu Tyr Thr Ile Lys
450                 455                 460

Val Ile Val Asp His Glu Lys Val Phe Lys Gly Ser Asp Gln Ser Arg
465                 470                 475                 480

Lys Ser Tyr Leu Tyr His Ile Gln Trp Leu Gly Tyr Pro Asp Glu Thr
                485                 490                 495

Trp Glu Pro Tyr Glu His Leu Asp Asp Cys Gln Val Phe Glu Asp Tyr
            500                 505                 510

Leu Lys His His Asn Ile Ser Leu Phe Asp Glu Glu Glu Asp Arg
        515                 520                 525
```

```
Lys Val Asp Asp Ser Met Leu Leu Pro Ala Trp Met His Glu Asp Glu
        530                 535                 540

Ser Leu Phe Glu Ala Leu Leu Pro Ile Ile Cys Cys Ser Thr Asp Asn
545                 550                 555                 560

Pro Arg His His Leu Asp Asp Val Pro Pro Phe Asp Phe Asn Tyr
                565                 570                 575

<210> SEQ ID NO 9
<211> LENGTH: 253
<212> TYPE: PRT
<213> ORGANISM: Naegleria gruberi

<400> SEQUENCE: 9

Met Thr Glu Ile Val Glu Leu Ser Asn Ile Glu Pro Lys Asp Gln Lys
1               5                   10                  15

Gln Ala Ile Ile Gly Gly Thr Trp Asn Arg Tyr Gly Asn Ser Ile Glu
            20                  25                  30

Ile Val Ala Gly Ile Ser Asp Glu Asn Asn Thr Leu Leu Asp Asn Leu
        35                  40                  45

Thr Asn Cys Cys Glu Ser Phe Val Leu Asp Lys Leu Trp His Leu Asn
50                  55                  60

Arg Ser Met Tyr Asn Lys Leu Asp Thr Ile Glu Glu Lys Ile Lys Asn
65                  70                  75                  80

Phe Lys Thr Tyr Ala Lys Tyr Pro Ser Leu Ala Leu Asn Leu Leu Cys
                85                  90                  95

Lys Glu Asn Tyr Asn Gly Lys Val Lys Pro Tyr Arg Lys His Ile Asp
            100                 105                 110

Pro Asn Asn Asn Gly Met Asp Val Leu Met Phe Phe Gly Lys Thr Phe
        115                 120                 125

Glu Gly Gly Asn Leu Ile Val Ser Tyr His Tyr Thr Asn Ile Asp Phe
130                 135                 140

Arg Met Phe Thr Leu Pro Ile Gln Ser Gly Asp Leu Val Phe Leu Asn
145                 150                 155                 160

Ser Arg Ile Tyr His His Lys Val Thr Lys Val Thr Ser Gly Val Arg
                165                 170                 175

Cys Gly Leu Val Phe Phe Ala Gly Leu Asp His Phe Ser Val Arg Lys
            180                 185                 190

Ala Asn Tyr Lys Lys Val Lys Lys Glu Glu Tyr Gln Lys Asn Met Asp
        195                 200                 205

Asp Lys Leu Leu Ala Leu Pro Phe Gln Gln Lys Asp Lys Asp Leu Arg
210                 215                 220

Ile Glu Arg Thr Lys Thr Gly Arg Lys Glu Ile Lys Gln Phe His Lys
225                 230                 235                 240

Asn Leu Gln Asn Asn Leu Pro Asn Lys Lys Arg Lys Lys
                245                 250

<210> SEQ ID NO 10
<211> LENGTH: 60
<212> TYPE: DNA
<213> ORGANISM: Artificial Sequence
<220> FEATURE:
<223> OTHER INFORMATION: Synthetic construct

<400> SEQUENCE: 10
attacacgcg cgatatcgtt aacgataatt cgcgcgatta cgatcgataa cgcgttaata    60
```

```
<210> SEQ ID NO 11
<211> LENGTH: 55
<212> TYPE: DNA
<213> ORGANISM: Artificial Sequence
<220> FEATURE:
<223> OTHER INFORMATION: Synthetic construct

<400> SEQUENCE: 11
cggcgtttcc gggttccata ggctccgccc cggactctga tgaccagggc atcac         55

<210> SEQ ID NO 12
<211> LENGTH: 1766
<212> TYPE: DNA
<213> ORGANISM: Artificial Sequence
<220> FEATURE:
<223> OTHER INFORMATION: Synthetic construct

<400> SEQUENCE: 12
gggtctagaa ataattttgt ttaactttaa gaaggagata tacatatgaa aatcgaagaa      60
ggtaaaggtc accatcacca tcaccacgga tccatggaag acgccaaaaa cataaagaaa     120
ggcccggcgc cattctatcc tctagaggat ggaaccgctg agagcaact gcataaggct      180 atgaagagat acgccctggt tcctggaaca attgctttta cagatgcaca tatcgaggtg     240
aacatcacgt acgcggaata cttcgaaatg tccgttcggt tggcagaagc tatgaaacga     300
tatgggctga atacaaatca cagaatcgtc gtatgcagtg aaaactctct tcaattcttt     360
atgccggtgt tgggcgcgtt atttatcgga gttgcagttg cgcccgcgaa cgacatttat     420
aatgaacgtg aattgctcaa cagtatgaac atttcgcagc ctaccgtagt gtttgtttcc     480
aaaaaggggt tgcaaaaaat tttgaacgtg caaaaaaaat taccaataat ccagaaaatt     540
attatcatgg attctaaaac ggattaccag ggatttcagt cgatgtacac gttcgtcaca     600
tctcatctac ctcccggttt taatgaatac gattttgtac cagagtcctt tgatcgtgac     660
aaaacaattg cactgataat gaattcctct ggatctactg ggttacctaa gggtgtggcc     720
cttccgcata gaactgcctg cgtcagattc tcgcatgcca gagatcctat ttttggcaat     780
caaatcattc cggatactgc gattttaagt gttgttccat tccatcacgg ttttggaatg     840
tttactacac tcggatattt gatatgtgga tttcgagtcg tcttaatgta tagatttgaa     900
gaagagctgt ttttacgatc ccttcaggat tacaaaattc aaagtgcgtt gctagtacca     960
acctattttt cattcttcgc caaaagcact ctgattgaca aatacgattt atctaattta    1020
cacgaaattg cttctggggg cgcacctctt tcgaaagaag tcggggaagc ggttgcaaaa    1080
cgcttccatc ttccagggat acgacaagga tatgggctca ctgagactac atcagctatt    1140
ctgattacac ccgaggggga tgataaaccg ggcgcggtcg gtaaagttgt tccattttt    1200 gaagcgaagg ttgtggatct ggataccggg aaaacgctgg gcgttaatca gagaggcgaa    1260
ttatgtgtca gaggacctat gattatgtcc ggttatgtaa acaatccgga agcgaccaac    1320
gccttgattg acaaggatgg atggctacat tctggagaca tagcttactg ggacgaagac    1380
gaacacttct tcatagttga ccgcttgaag tctttaatta aatacaaagg atatcaggtg    1440
gcccccgctg aattggaatc gatattgtta caacacccca acatcttcga cgcgggcgtg    1500
gcaggtcttc ccgacgatga cgccggtgaa cttcccgccg ccgttgttgt tttggagcac    1560
ggaaagacga tgacggaaaa agagatcgtg gattacgtcg ccagtcaagt aacaaccgcg    1620
aaaaagttgc gcggaggagt tgtgtttgtg gacgaagtac cgaaaggtct taccggaaaa    1680
```

```
ctcgacgcaa gaaaaatcag agagatcctc ataaaggcca agaagggcgg aaagtccaaa    1740
ctcgagtaag gttaacctgc aggagg                                         1766
```